(12) United States Patent
Mercenier et al.

(10) Patent No.: US 8,961,952 B2
(45) Date of Patent: *Feb. 24, 2015

(54) EXTRUDED NON-REPLICATING PROBIOTIC MICRO-ORGANISMS AND THEIR HEALTH BENEFITS

(75) Inventors: Annick Mercenier, Bussigny (CH); Antoine Wermeille, Lausanne (CH); Audrey Demont, Prilly (CH); Guenolee Prioult, Bern (CH)

(73) Assignee: Nestec S.A., Vevey (CH)

( * ) Notice: Subject to any disclaimer, the term of this patent is extended or adjusted under 35 U.S.C. 154(b) by 16 days.

This patent is subject to a terminal disclaimer.

(21) Appl. No.: 13/884,543

(22) PCT Filed: Nov. 11, 2011

(86) PCT No.: PCT/EP2011/069906
§ 371 (c)(1),
(2), (4) Date: May 9, 2013

(87) PCT Pub. No.: WO2012/062895
PCT Pub. Date: May 18, 2012

(65) Prior Publication Data
US 2013/0230611 A1  Sep. 5, 2013

(30) Foreign Application Priority Data
Nov. 11, 2010  (EP) .................................... 10190892

(51) Int. Cl.
| | |
|---|---|
| *A01N 63/00* | (2006.01) |
| *A01N 63/02* | (2006.01) |
| *A61K 35/00* | (2006.01) |
| *A23K 1/00* | (2006.01) |
| *A23L 1/00* | (2006.01) |
| *A23L 1/30* | (2006.01) |
| *A61Q 19/00* | (2006.01) |
| *A61K 8/99* | (2006.01) |

(52) U.S. Cl.
CPC ............. *A61K 35/744* (2013.01); *A23K 1/003* (2013.01); *A23K 1/008* (2013.01); *A23K 1/009* (2013.01); *A23L 1/0079* (2013.01); *A23L 1/3014* (2013.01); *A61Q 19/00* (2013.01); *A61K 8/99* (2013.01); *A61K 35/742* (2013.01); *A61K 35/745* (2013.01); *A61K 35/747* (2013.01); *A23V 2002/00* (2013.01); *A61K 2800/10* (2013.01)

USPC .................... 424/93.44; 424/93.4; 424/93.45; 424/93.48; 424/780

(58) Field of Classification Search
None
See application file for complete search history.

(56) References Cited

U.S. PATENT DOCUMENTS

| | | | |
|---|---|---|---|
| 2004/0047896 A1* | 3/2004 | Malnoe et al. ................ | 424/439 |
| 2004/0197277 A1* | 10/2004 | Gonzales ........................ | 424/48 |
| 2005/0180962 A1* | 8/2005 | Raz et al. .................... | 424/93.45 |
| 2008/0206212 A1* | 8/2008 | McMahon et al. ......... | 424/93.45 |
| 2009/0296674 A1 | 12/2009 | Ekl et al. | |
| 2009/0297664 A1 | 12/2009 | Forte et al. | |
| 2010/0009009 A1* | 1/2010 | Young et al. .................. | 424/613 |
| 2012/0230956 A1* | 9/2012 | McLean et al. .............. | 424/93.4 |

FOREIGN PATENT DOCUMENTS

| | | | |
|---|---|---|---|
| CN | 101810258 | | 8/2010 |
| WO | 0162099 | | 8/2001 |
| WO | 2004069156 | | 8/2004 |
| WO | 2006108824 | | 10/2006 |
| WO | WO 2006108824 A1 * | | 10/2006 |
| WO | 2007019901 | | 2/2007 |
| WO | 2007059588 | | 5/2007 |
| WO | WO 2007059588 | * | 5/2007 |
| WO | 2010000776 | | 1/2010 |
| WO | 2010008879 | | 1/2010 |
| WO | WO 2010000776 | * | 1/2010 |
| WO | WO 2010008879 | * | 1/2010 |

OTHER PUBLICATIONS

Simons et al., Abstract—J Am Geriatr Soc. Aug. 2002;50(8):1454-5.*
Simons, The effect of medicated chewing gums on oral health in frail older people: a 1-year clinical trial. J. Am. Geriatr Soc. Aug. 2002. 50(8): 1454-5.

\* cited by examiner

*Primary Examiner* — Chris R Tate
*Assistant Examiner* — Douglas F White
(74) *Attorney, Agent, or Firm* — K&L Gates LLP

(57) ABSTRACT

The present invention generally relates to the field of probiotic micro-organisms, in particular to the field of non-replicating probiotic micro-organisms. Embodiments of the present invention relate to compositions comprising probiotic micro-organisms that were rendered non-replicating by extrusion. Such compositions may be used to treat or prevent disorders that are related to a compromised immune system.

5 Claims, 19 Drawing Sheets

Extruded control (100x)

Extruded control (40x)

Extruded B. longum NCC3001
110°C, 100x

Extruded B. longum NCC3001
110°C, 40x

Cold extruded control (without bacteria)

500rpm (100x)

1200rpm (100x)

85°C (100x)

140°C (100x)

Live *B. longum* (NCC3001) (100x)

Cold extruded *B. longum* (NCC3001)

500rpm (100x)

1200rpm (100x)

Extruded *B. longum* (NCC3001)

85°C (100x)

140°C (100x)

Live *B. lactis* (BL818) (100x)

Cold extruded *B. lactis* (BL818)

500rpm (100x)            1200rpm (100x)

Extruded *B. lactis* (BL818)

85°C (100x)            140°C (100x)

Live *L. paracasei* (ST11)

Cold extruded *L. paracasei* (ST11)

500rpm (100x)     1200rpm (100x)

Extruded *L. paracasei* (ST11)

85°C (100x)      140°C (100x)

Fig: *B. longum* (NCC3001)
Primers NCC3001A/B 1. gDNA NCC3001 +ctrl
2. NTC -ctrl
3. SmartLadder SF Eurogentec
4. -Ctrl extraction
5. -Ctrl extruded 100°C
6. -Ctrl extruded 100°C spiked NCC3001
7. NCC3001 extruded 100°C
8. NCC3001 extruded 130°C
9. SmartLadder SF Eurogentec

EXTRUDED NON-REPLICATING PROBIOTIC MICRO-ORGANISMS AND THEIR HEALTH BENEFITS

CROSS REFERENCE TO RELATED APPLICATIONS

The present application is a National Stage of International Application No. PCT/EP2011/069906, filed on Nov. 11, 2011, which claims priority to European Patent Application No. 10190892.9, filed Nov. 11, 2010, the entire contents of which are being incorporated herein by reference.

The present invention generally relates to the field of probiotic micro-organisms, in particular to the field of non-replicating probiotic micro-organisms. Embodiments of the present invention relate to compositions comprising probiotic micro-organisms that were rendered non-replicating by extrusion. Such compositions may be used to treat or prevent disorders that are related to a compromised immune defense.

Probiotics may be defined as "Live microorganisms which when administered in adequate amounts confer a health benefit on the host" [FAO/WHO (2001) Health and Nutritional Properties of Probiotics in Food including Powder Milk with Live Lactic Acid Bacteria. Report of a Joint FAO/WHO Expert Consultation on Evaluation of Health and Nutritional Properties of Probiotics in Food Including Powder Milk with Live Lactic Acid Bacteria]. Therefore, the vast majority of published literature deals with living probiotics. However, several studies investigated the health benefits delivered by non-replicating bacteria but came to the conclusion that heat-inactivation of probiotics generally leads to a loss of their purported health benefit (Rachmilewitz, D., K. et al, 2004, Gastroenterology 126:520-528; Castagliuolo, I., et al., 2005, FEMS Immunol. Med. Microbiol. 43:197-204; Gill, H. S, and K. J. Rutherfurd. 2001, Br. J. Nutr. 86:285-289; Kaila, M., et al., 1995, Arch. Dis. Child 72:51-53; Wagner, R. D., et al., 2000, J. Food Prot. 63:638-644).

Some studies, however, showed that killed probiotics may retain some health effects. This may depend for example on the method used to inactivate them (Rachmilewitz, D., K. et al, 2004, Gastroenterology 126:520-528; Gill, H. S, and K. J. Rutherfurd. 2001, Br. J. Nutr. 86:285-289). The technologies used in the literature to kill probiotic strains are mostly heat-treatment, γ-irradiation, UV-treatment or chemical agents (formalin, paraformaldehyde).

Being able to use non-replicating probiotics in food products would have several significant advantages. As providing food products with viable probiotics also after longer storing times is not a trivial task, the possibility to use non-replicating probiotics would eliminate any problems associated therewith.

Further, the range of products that could be supplemented with probiotics and the associated health benefits could be broadened significantly.

To be applicable to the food industry, however, the method used to render probiotics non-replicating must be applicable in an industrial scale. γ-irradiation, UV-treatment or the use of chemical agents might be problematic in this respect. Even heat treatments might not be easy to apply for some product categories.

Further, it would be desirable if the non replicating probiotic micro-organisms did not only retain a small part of their health effects but retained substantial parts or all of their health effects compared to their viable counterparts.

The present inventors have addressed these needs.

Consequently, it was the objective of the present invention to provide the art with a composition that can be easily produced in industrial scale for a very broad range of products and that contains non-replicating probiotic microorganisms with substantially the same or even improved or new health benefits compared with their live counterparts.

The present inventors have achieved this objective by the subject matter of the independent claim. The dependant claims further develop the idea of the present invention.

The present inventors were surprised to see that compositions comprising probiotic micro-organisms or dairy starters rendered non-replicating by extrusion are able to satisfy the needs described above.

Extrusion is a technique commonly used in the food industry today. It allows forming shapes by forcing a material through a region of high-temperature and/or pressure with concomitant shearing. The process parameters such as heat, pressure, mechanical shearing and optionally flash on extruded materials and the combinations thereof can be modulated to generate different types of final products. Extrusion allows generation of a variety of textures and shapes starting from various raw materials. Commonly, extruded materials include metals, polymers, ceramics and foodstuffs. Food products such as pastas, snack foods, breakfast cereals, ice-creams, confectionery and even some pet foods and ready-to-eat snacks including finger foods are mostly manufactured by extrusion.

An extruder may consist of a power supply to operate one or two screws, a feeder to meter in the raw ingredients, and a barrel, which surrounds the screws. The screws are designed to induce compression, to generate shear stresses and to convoy the raw material. Liquid ingredients and water can be injected into the barrel depending on the product being made. A cooking process may also take place within the extruder where the product produces its own friction and heat due to the pressure generated. Barrel section temperatures are controlled by induction belts for heating and by water circulation for cooling. Finally, the food ingredients are forced through towards a shaped hole, the die, which shapes the product to increase the variety of textures and shapes.

Two main advantages of extrusion processes over other manufacturing processes are their ability to create very complex cross-sections and the ability to work in a continuous process.

The present inventors have found, for example, that extruded *B. longum* NCC3001 shows a dose-response curve of cytokine production by human PBMC upon 36 h incubation.

Consequently, one embodiment of the present invention is a composition comprising non-replicating probiotic micro-organisms, wherein the probiotic micro-organisms were rendered non-replicating by extrusion.

"Non-replicating" probiotic micro-organisms include probiotic bacteria that are inactivated, dead, non-viable and/or present as fragments such as DNA, metabolites, cytoplasmic compounds, and/or cell wall materials.

"Non-replicating" means that no viable cells and/or colony forming units can be detected by classical plating methods. Such classical plating methods are summarized in the microbiology book: James Monroe Jay, Martin J. Loessner, David A. Golden. 2005. Modern food microbiology. 7th edition, Springer Science, New York, N.Y. 790 p. Typically, the absence of viable cells can be shown as follows: no visible colony on agar plates or no increasing turbidity in liquid growth medium after inoculation with different concentrations of bacterial preparations ('non replicating' samples) and incubation under appropriate conditions (aerobic and/or anaerobic atmosphere for at least 24 h).

Probiotics are defined for the purpose of the present invention as "Microbial cell preparations or components of microbial cells with a beneficial effect on the health or well-being of the host." (Salminen S, Ouwehand A. Benno Y. et al "Probiotics: how should they be defined" Trends Food Sci. Technol. 1999:10 107-10).

The possibility to use non-replicating probiotic micro-organisms offers several advantages. They can be easily applied to a broad range of products. The possibility to use extrusion to render probiotics non-replicating even further increases the number of products, non-replicating probiotic microorganisms—which still are bioactive—may be applied to. Problems with trying to keep probiotics viable until they are consumed or even until they arrive in the intestines can be circumvented.

Further, for example in severely immuno-compromised infants or young children, the use of live probiotics may be limited in exceptional cases due to a potential risk to develop bacteremia. Non-replicating probiotics may be used without any problem.

Additionally, the provision of non-replicating probiotic micro-organisms allows the hot reconstitution while retaining health benefits.

For example a matrix may be co-extruded with probiotic micro-organisms and the matrix can then be added to a broad range of products as ingredient. People skilled in the art will be able to determine appropriate matrices for such a procedure.

Alternatively, probiotic micro-organisms may be coextruded with a mix of raw materials to produce a final product directly.

Hence, in one embodiment the probiotic micro-organisms may be co-extruded with the composition.

Any kind of extrusion process is applicable for the purposes of the present invention. The preferred extrusion process depends on the desired composition and shape of the final product. People skilled in the art will be able to select extrusion processes appropriately. Marshall, R. T, et al. (2003), Ice cream, Kluwer Academic/Plenum Publishers, New York; Smith, J. S. & Hui, Y. H. (2004). Food processing: principles and applications. Blackwell Publishing Ltd., Oxford, UK; and Bouvier, J.-M. (2001). Breakfast cereals. In: Robin, G. editor, Extrusion cooking: technologies and applications, Woodhead Publishing Ltd., Cambridge, England; summarize extrusion techniques.

For example, the extrusion may be selected from the group consisting of low-temperature freezing extrusion, cold extrusion, extrusion cooking, or combinations thereof.

Low-temperature freezing extrusion is usually used to produce ice-creams or frozen yoghurts, for example, and is normally carried out at a temperature in the range of 0° C. to −20° C., for example at −15° C.

Cold extrusion may be used, e.g., to produce pasta and may be carried out at a temperature in the range of 20-90° C., e.g., 25-40° C. or 60-90° C., and with a moisture content of above 30 weight-% (for example between 30-40 weight-%). Under industrial conditions cold extrusion may be carried out at a production rate of 1000-8000 kg/h.

Extrusion cooking may be carried out under direct expansion conditions or under indirect expansion conditions.

Direct expansion may be used, e.g., to produce extruded breakfast cereals, pet food & fish feed. It may be carried out at a temperature above 100° C. (for example between 110° C. and 180° C., and at a moisture content of below 20 weight-% (for example between 16 weight-% and 20 weight-%). The screw speed may be between 200 rpm and 1300 rpm, for example between 200 rpm and 450 rpm; with a pressure at the die between 1-150 bars, for example 100-150 bar.

When using indirect expansion the extruder may be used to cook a dough, followed by pellet forming, flaking, toasting and/or coating. This method may be used to produce snacks and breakfast cereals, for example. It is carried out at a temperature of above 100° C., with a moisture content in the range of 22-26 weight-%. The screw speed may be below 200 rpm.

In particular in the case of cold extrusion or extrusion cooking the probiotic microorganisms may be either provided as part of the dry mix of raw materials or as part of the wet mix that is added to the dry mix in the extrusion step. FIGS. 1 and 2 illustrate examples of both processes. Of course, probiotic microorganisms may also be added to the dry mix and to the wet mix.

Hence, in one embodiment the composition of the present invention may be obtainable, or may be obtained, by a process comprising adding probiotic micro-organisms to a raw material, extruding the dry mix under water addition, and recovering the extruded material comprising the non replicating probiotic micro-organisms.

In an alternative embodiment, the composition of the present invention may be obtainable, or may be obtained, by a process comprising transforming a raw material into a dry mix, adding a wet mix comprising water and probiotic micro-organisms during an extrusion step to the dry mix, and recovering the extruded material comprising the non replicating probiotic micro-organisms.

Combinations of both processes are feasible.

The composition of the present invention may be a final product or may me an ingredient that may be used to prepare products.

The extrusion step may be carried out at a temperature in the range of −20° C. to 0° C., in the range of 15° C. to 45° C., in the range of 60° C. to 90° C., in the range of 90° C. to 130° C., or in the range of 110° C. to 180° C., for example 85° C. to 160° C. or 110 to 130° C. The water content at the extrusion step may be in the range of 30-40 weight-%, or 16-20 weight-%. The pressure at the die may be in the range of 1-200 bar, for example 50-200 bar, 100-150 bar or, for example, 55-125 bar in extrusion and 1-55 bar in cold extrusion.

Any raw material can be used. The choice of raw material will vary widely and will depend on the final product. People skilled in the art will be able to select appropriate raw materials.

For example for cereal products the raw materials may include flour, starch or derivatives, sugar, salt, malt extract or other sweeteners, heat stable vitamins, minerals, flavorings, and/or colorants.

For pet food products, the raw material may include grain, meat, a lipid source, vitamins, and/or minerals.

For pasta products, the raw materials may include semolina, a mix of semolina and flour, and/or egg yolk.

For ice cream products the raw materials may include eggs, milk, cream, sugar, and/or flavorings.

For frozen yoghurt products the raw materials may include yoghurt, sugar, and or flavorings.

Probiotic microorganisms may be added to the extrusion process in an amount that the final product will contain non replicating probiotic micro-organisms in an amount corresponding to about $10^6$ to $10^{12}$ equivalent cfu/serving.

Hence, for compositions which are ingredients for further products, the amount of probiotics to be added should be higher.

The composition according to the present invention may comprise non replicating probiotic micro-organisms in any effective amount, for example in an amount corresponding to about $10^6$ to $10^{12}$ equivalent cfu/serving.

The compositions of the present invention comprise non-replicating probiotic micro-organisms in an amount sufficient to at least partially produce a health benefit. An amount adequate to accomplish this is defined as "a therapeutically effective dose". Amounts effective for this purpose will depend on a number of factors known to those of skill in the art such as the weight and general health state, and on the effect of the food matrix.

In prophylactic applications, compositions according to the invention are administered to a person susceptible to or otherwise at risk of a disorder in an amount that is sufficient to at least partially reduce the risk of developing that disorder. Such an amount is defined to be "a prophylactic effective dose". Again, the precise amounts depend on a number of factors such as the state of health and weight, and on the effect of the food matrix.

Those skilled in the art will be able to adjust the therapeutically effective dose and/or the prophylactic effective dose appropriately.

In general the composition of the present invention contains non-replicating probiotic micro-organisms in a therapeutically effective dose and/or in a prophylactic effective dose.

Typically, the therapeutically effective dose and/or the prophylactic effective dose may be the range of about 0.005 mg-1000 mg non-replicating, probiotic micro-organisms per daily dose.

In terms of numerical amounts, the extruded non-replicating micro-organisms may be present in the composition in an amount corresponding to between $10^4$ and $10^{12}$ equivalent cfu/g of the dry composition. Obviously, non-replicating micro-organisms do not form colonies, consequently, this term is to be understood as the amount of non replicating micro-organisms that is obtained from $10^4$ and $10^{12}$ cfu/g replicating bacteria. This includes micro-organisms that are inactivated, non-viable or dead or present as fragments such as DNA or cell wall or cytoplasmic compounds. In other words, the quantity of micro-organisms which the composition contains is expressed in terms of the colony forming ability (cfu) of that quantity of micro-organisms as if all the micro-organisms were alive irrespective of whether they are, in fact, non replicating, such as inactivated or dead, fragmented or a mixture of any or all of these states.

Preferably the non-replicating micro-organisms are present in an amount equivalent to between $10^4$ to $10^9$ cfu/g of dry composition, even more preferably in an amount equivalent to between $10^5$ and $10^9$ cfu/g of dry composition.

Any amount of non-replicating micro-organisms will be effective. However, it is generally preferred, if at least 90%, preferably, at least 95%, more preferably at least 98%, most preferably at least 99%, ideally at least 99.9%, most ideally all of the probiotics are non-replicating.

In one embodiment of the present invention all micro-organisms are non-replicating.

Consequently, in the composition of the present invention at least 90%, preferably, at least 95%, more preferably at least 98%, most preferably at least 99%, ideally at least 99.9%, most ideally all of the probiotics are non-replicating.

All probiotic micro-organisms may be used for the purpose of the present invention.

For example, the probiotic micro-organisms may be selected from the group consisting of bifidobacteria, lactobacilli, propionibacteria, streptococci, lactococci enterococci and *Escherichia* or combinations thereof, for example *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactobacillus lactis, Lactobacillus helveticus, Streptococcus thermophilus, Lactococcus lactis, Lactococcus diacetylactis, Lactococcus cremoris, Lactobacillus bulgaricus, Lactobacillus helveticus, Lactobacillus delbrueckii, Escherichia coli* and/or mixtures thereof.

The composition in accordance with the present invention may, for example comprise non-replicating probiotic micro-organisms selected from the group consisting of *Bifidobacterium longum* NCC 3001, *Bifidobacterium longum* NCC 2705, *Bifidobacterium breve* NCC 2950, *Bifidobacterium lactis* NCC 2818, *Bifidobacterium lactis* Bb12, *Lactobacillus johnsonii* NCC 533, *Lactobacillus paracasei* NCC 2461, *Lactobacillus rhamnosus* NCC 4007, *Lactobacillus reuteri* DSM17983, *Lactobacillus reuteri* ATCC55730, *Streptococcus thermophilus* NCC 2019, *Streptococcus thermophilus* NCC 2059, *Lactobacillus casei* NCC 4006, *Lactobacillus acidophilus* NCC 3009, *Lactobacillus casei* ACA-DC 6002 (NCC 1825), *Escherichia coli* Nissle, *Lactobacillus bulgaricus* NCC 15, *Lactococcus lactis* NCC 2287, or combinations thereof.

All these strains were either deposited under the Budapest treaty and/or are commercially available The strains have been deposited under the Budapest treaty as follows:

*Bifidobacterium longum* NCC 3001: ATCC BAA-999 (isolated June 1969)
*Bifidobacterium longum* NCC 2705: CNCM I-2618 (deposited 29.01.2001)
*Bifidobacterium breve* NCC 2950 CNCM I-3865 (deposited 15.11.2007)
*Bifidobacterium lactis* NCC 2818: CNCM I-3446 (deposited 07.06.2005)
*Lactobacillus paracasei* NCC 2461: CNCM I-2116 (deposited 12.01.1999)
*Lactobacillus rhamnosus* NCC 4007: CGMCC 1.3724 (deposited October 2004)
*Streptococcus themophilus* NCC 2019: CNCM I-1422 (deposited 10.05.1994)
*Streptococcus themophilus* NCC 2059: CNCM I-4153 (deposited 24.04.2009)
*Lactococcus lactis* NCC 2287: CNCM I-4154 (deposited 24.04.2009)
*Lactobacillus casei* NCC 4006: CNCM I-1518 (deposited 30.12.1994)
*Lactobacillus casei* NCC 1825: ACA-DC 6002
*Lactobacillus acidophilus* NCC 3009: ATCC 700396
*Lactobacillus bulgaricus* NCC 15: CNCM I-1198 (deposited 02.04.1992)
*Lactobacillus johnsonii* La1 CNCM I-1225 (deposited 30.06.1992)
*Lactobacillus reuteri* DSM17938 DSM17938 (deposited 06.02.2006)
*Lactobacillus reuteri* ATCC55730 ATCC55730 (deposited 07.12.1995)
*Escherichia coli* Nissle 1917: DSM 6601 (deposited 11.07.1991)

Strains named ATCC were deposited with the ATCC Patent Depository, 10801 University Blvd., Manassas, Va. 20110, USA.

Strains named CNCM were deposited with the COLLECTION NATIONALE DE CULTURES DE MICROORGANISMES (CNCM), 25 rue du Docteur Roux, F-75724 PARIS Cedex 15, France.

Strains named CGMCC were deposited with the China General Microbiological Culture Collection Center, Institute of Microbiology, Chinese Academy of Sciences, Zhongguancun, P.O. Box 2714, Beijing 100080, China.

Strains named ACA-DC were deposited with the Greek Coordinated Collections of Microorganisms, Dairy Laboratory, Department of Food Science and Technology, Agricultural University of Athens, 75, Iera odos, Botanikos, Athens, 118 55, Greece.

Strains named DSM were deposited with the DSMZ-Deutsche Sammlung von Mikroorganismen and Zellkulturen GmbH, Inhoffenstr. 7 B, 38124 Braunschweig, GERMANY.

The composition of the present invention may be any composition. For example, the composition may be selected from the group consisting of food products, pet food products, cereals, nutritional compositions, nutraceuticals, cosmetic compositions, food additives, cosmetic compositions, nutritional supplements and/or deserts.

The present inventors were able to demonstrate that the extrusion of probiotic microorganisms leads to non replicating probiotic microorganisms that are still bioactive. In particular, they show strong immune stimulating activities, enhanced or new compared to the corresponding viable probiotic microorganisms.

Consequently, the composition of the present invention may be for use in the treatment or prevention of disorders related to a compromised or challenged immune system.

The present invention also extends to the use of probiotic microorganisms that were rendered non-replicating by extrusion for the preparation of a composition to treat or prevent disorders related to a compromised or challenged immune system.

The immune boosting effects of non-replicating probiotics were confirmed by in vitro immunoprofiling. The in vitro model uses cytokine profiling from human Peripheral Blood Mononuclear Cells (PBMCs) and is well accepted in the art as standard model for tests of immunomodulating compounds (Schultz et al., 2003, Journal of Dairy Research 70, 165-173; Taylor et al., 2006, Clinical and Experimental Allergy, 36, 1227-1235; Kekkonen et al., 2008, World Journal of Gastroenterology, 14, 1192-1203)

The in vitro PBMC assay has been used by several authors/research teams for example to classify probiotics according to their immune profile, i.e. their anti- or pro-inflammatory characteristics (Kekkonen et al., 2008, World Journal of Gastroenterology, 14, 1192-1203). For example, this assay has been shown to allow prediction of an anti-inflammatory effect of probiotic candidates in mouse models of intestinal colitis (Foligne, B., et al., 2007, World J. Gastroenterol. 13:236-243). Moreover, this assay is regularly used as read-out in clinical trials and was shown to lead to results coherent with the clinical outcomes (Schultz et al., 2003, Journal of Dairy Research 70, 165-173; Taylor et al., 2006, Clinical and Experimental Allergy, 36, 1227-1235).

Allergic diseases have steadily increased over the past decades and they are currently considered as epidemics by WHO. In a general way, allergy is considered to result from an imbalance between the Th1 and Th2 responses of the immune system leading to a strong bias towards the production of Th2 mediators. Therefore, allergy can be mitigated, down-regulated or prevented by restoring an appropriate balance between the Th1 and Th2 arms of the immune system. This implies the necessity to reduce the Th2 responses or to enhance, at least transiently, the Th1 responses. The latter would be characteristic of an immune boost response, often accompanied by for example higher levels of IFNγ, TNF-α and IL-12. (Kekkonen et al., 2008, World Journal of Gastroenterology, 14, 1192-1203; Viljanen M. et al., 2005, Allergy, 60, 494-500)

Hence, the disorder linked to a compromised immune defense may be selected from the group consisting of infections, in particular bacterial, viral, fungal and/or parasite infections, for example respiratory tract infections, or gastrointestinal infections; phagocyte deficiencies; low to severe immunodepression levels such as those induced by stress or immunodepressive drugs, chemotherapy or radiotherapy; natural states of less immunocompetent immune systems such as those of the neonates or elderly; allergies; inflammatory disorders and combinations thereof.

As the immune system is usually less competent in neonates or in elderly, the compositions of the present invention may be in particularly useful for these groups.

The immune system of children usually faces a lot of challenges due to close contacts with other children in school or daycare.

Children are up to 18 years old, young children are up to 12 years old and infants are children of less than 12 months.

Elderly are people having surpassed the first ¾ of their expected life span.

Accordingly, the compositions of the present invention may be to be administered to children, e.g., young children or infants, the elderly or pets.

Further as most challenges to the immune system occur during the day it may be preferred to consume the compositions of the present invention in the morning to be well prepared for upcoming challenges to the immune system.

Hence, the composition of the present invention may be to be administered in the morning.

Those skilled in the art will understand that they can freely combine all features of the present invention described herein, without departing from the scope of the invention as disclosed. In particular, features described for the composition of the present invention may be applied to the use of the present invention and vice versa.

Further advantages and features of the present invention are apparent from the following Examples and Figures.

Figure 4:
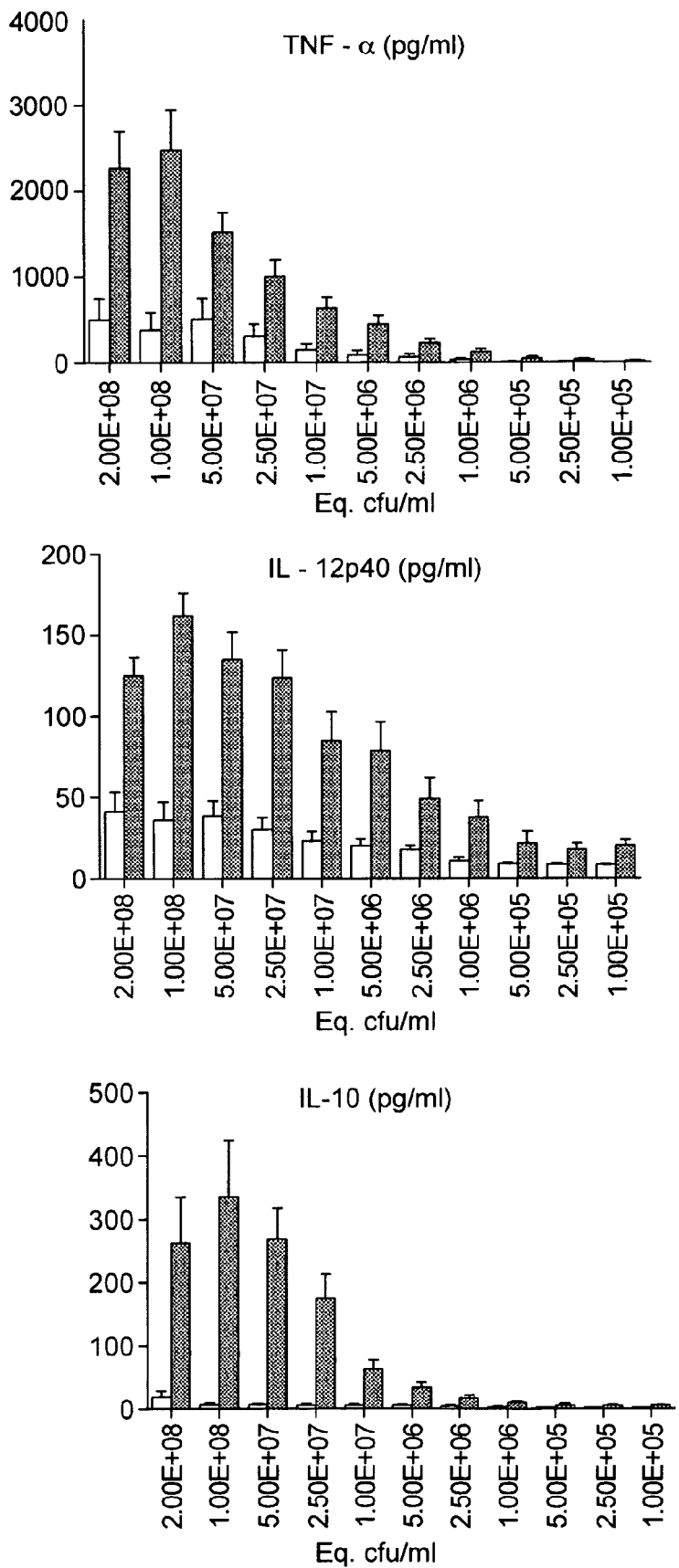

FIG. 4 shows a dose-response curve of cytokine production by human PBMC upon 36 h incubation with extruded *B. longum* NCC3001 samples generated at 130° C. (black bars) and extruded control (grey bars). Cytokines were measured by multiplex assay. Results are means+/−SEM of 4 individual donors.

Figure 5:
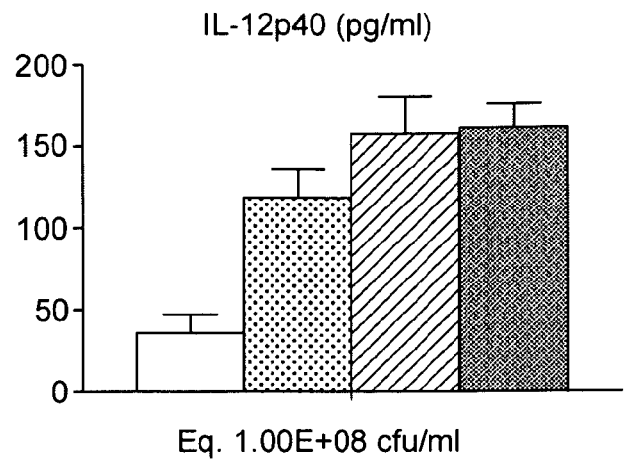
Figure 5:
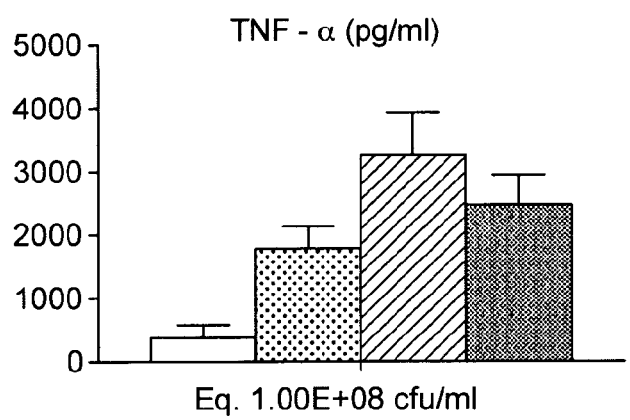
Figure 5:
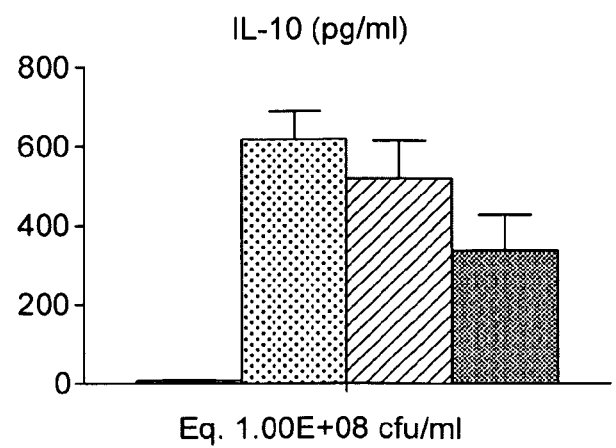

FIG. 5 shows the cytokine production by human PBMC upon 36 h incubation with extruded probiotics (*B. longum* NCC3001) and extruded control. Bacteria were extruded at 110° C. (grey bars), 120° C. (hatched bars) or 130° C. (black bars). Extruded control (open bars). Cytokines were measured by multiplex assay. Results are means+/−SEM of 4 individual donors.

Figure 6:
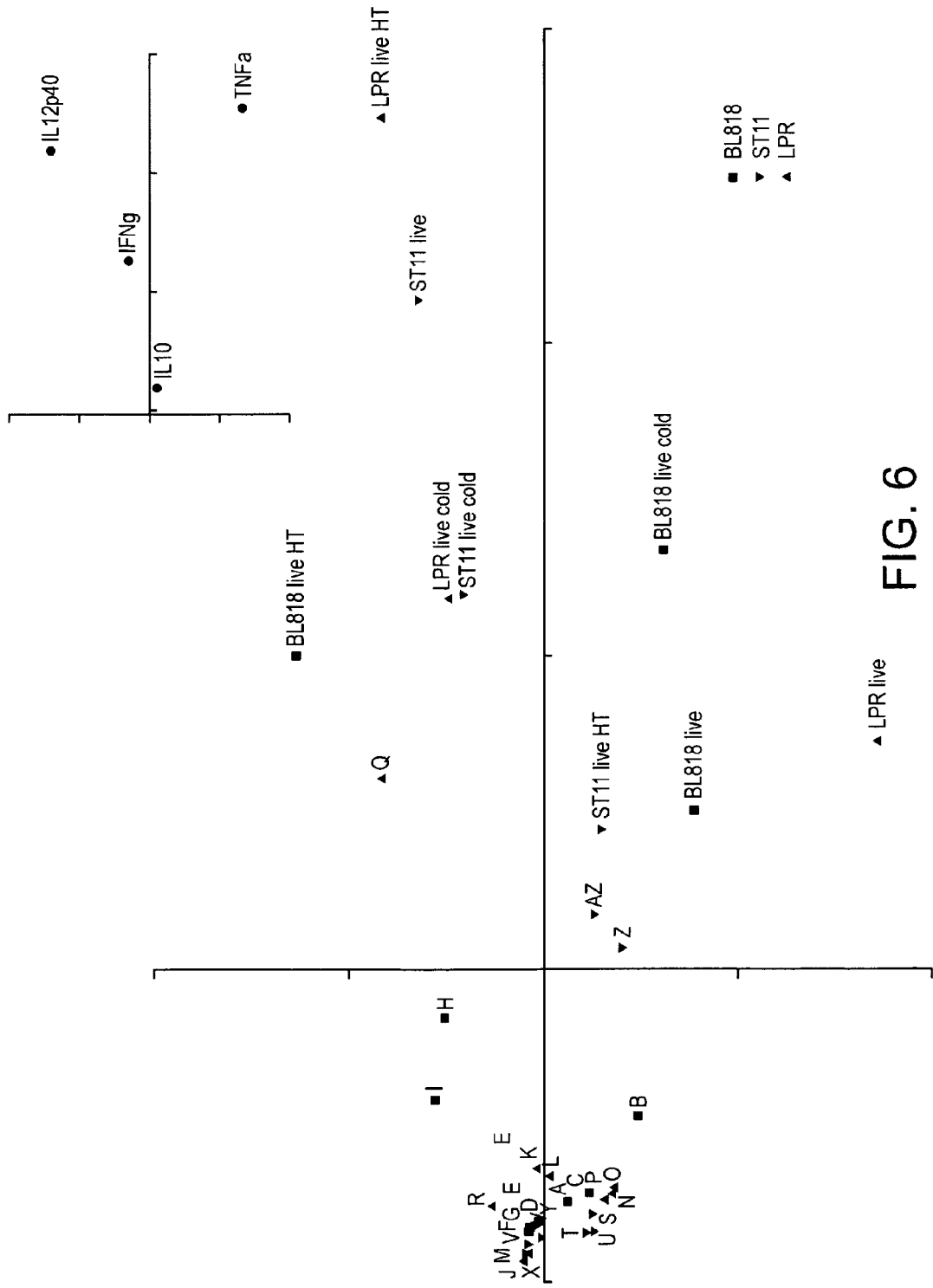

FIG. 6 shows the results of a PCA analysis of cytokine profiles of several extruded samples. Legend: A:BL818 800 rpm, B:BL818 1000 rpm, C:BL818 1200 rpm, D:BL818 85° C., E:BL818 100° C., F:BL818 120° C., G:BL818 140° C., H:BL818 120° C./15", I:BL818 140° C./15", J:LPR 800 rpm, K:LPR 1000 rpm, L:LPR 1200 rpm, M:LPR 85° C., N:LPR 100° C., O:LPR 120° C., P:LPR 140° C., Q:LPR 120° C./15", R:LPR 140° C./15", S:ST11 800 rpm, T:ST11 1000 rpm, U:ST11 1200 rpm, V:ST11 85° C., W:ST11 100° C., X:ST11 120° C., Y:ST11 140° C., Z:ST11 120° C./15", AZ:ST11 140° C./15".

Figure 7:
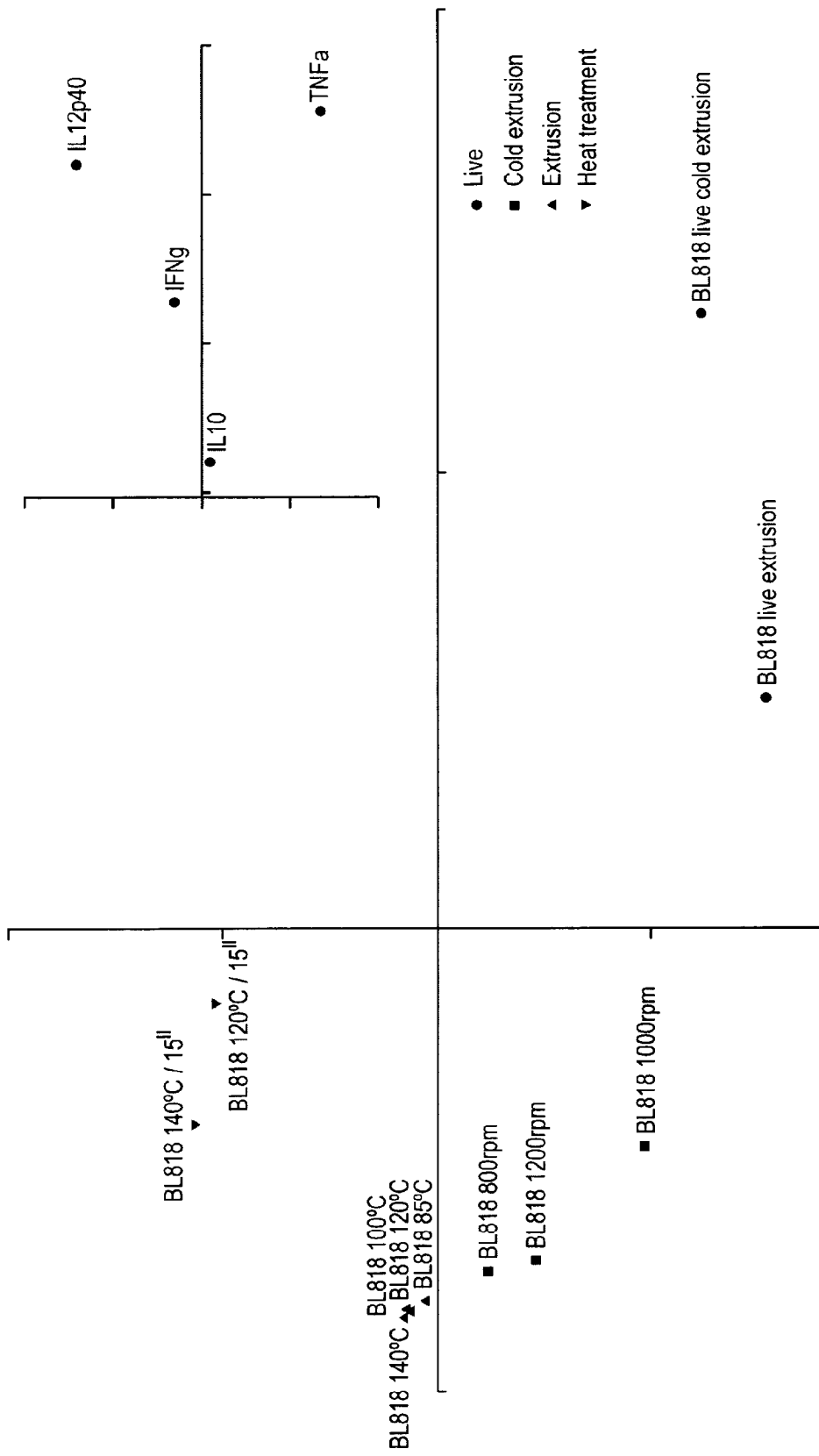

FIG. 7 shows the results of a PCA analysis on cytokine profiles for different extruded preparations of *B. longum* BL818.

Figure 8:
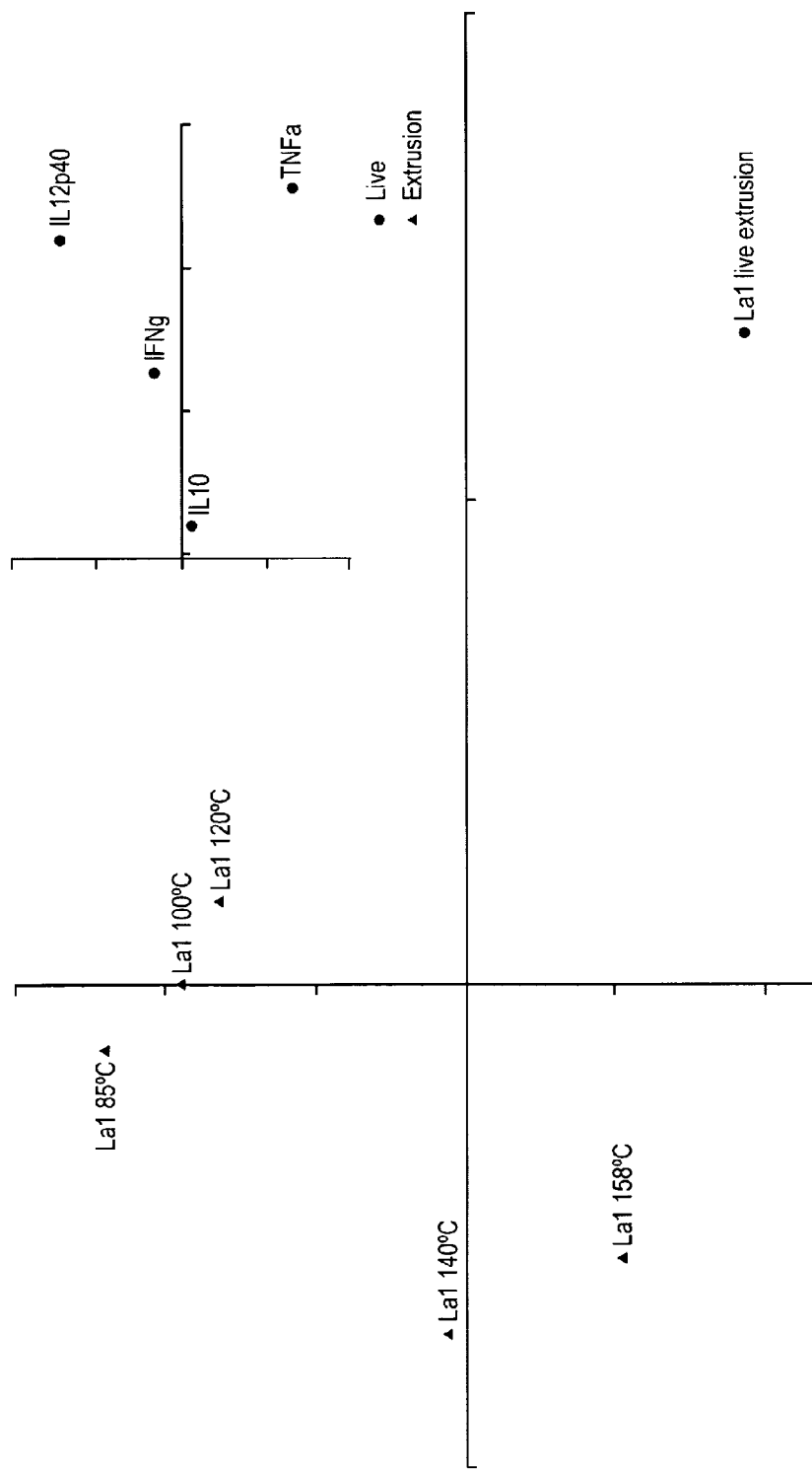

FIG. 8 shows the results of a PCA analysis on cytokine profiles for different extruded preparations of *L. johnsonii* La1.

Figure 9:
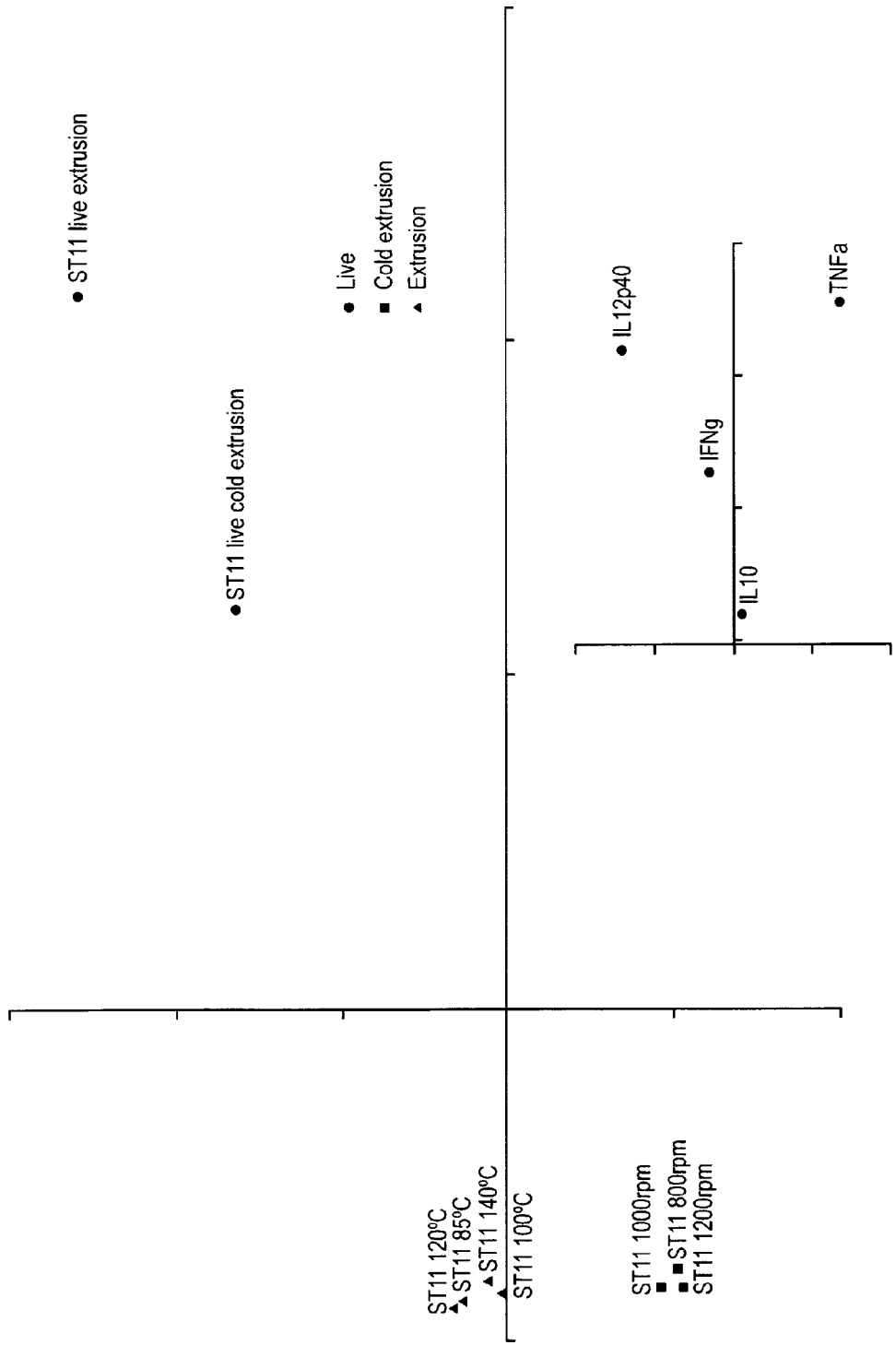
Figure 10A:
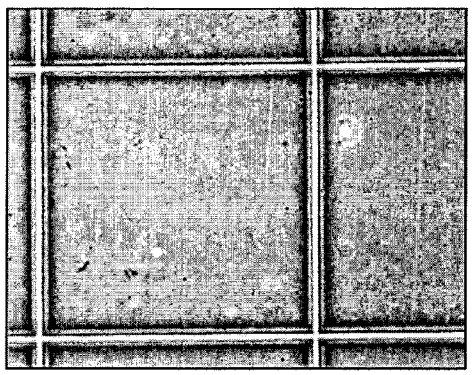
Figure 10A:
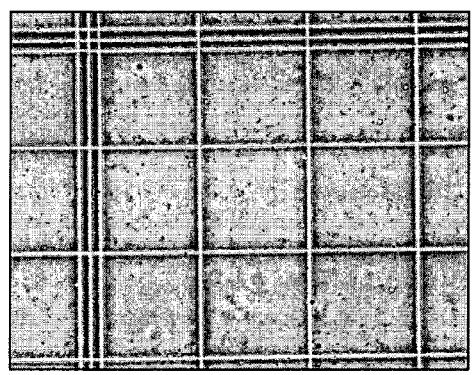
Figure 10A:
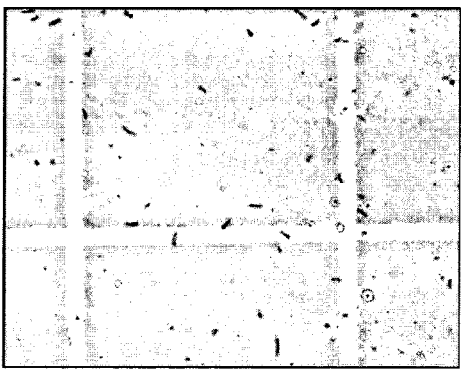
Figure 10A:
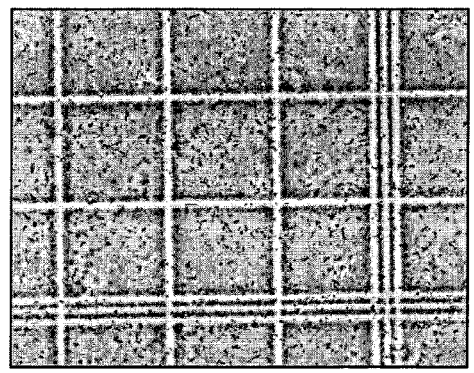
Figure 10B:
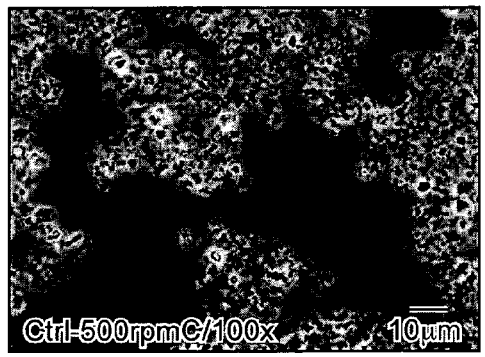
Figure 10B:
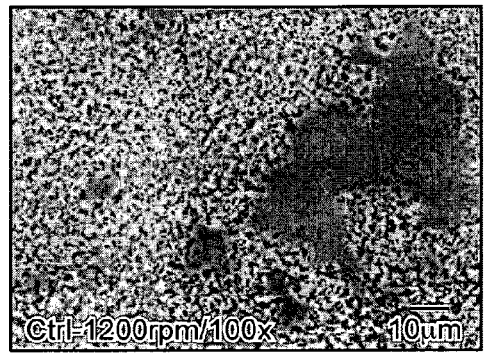
Figure 10B:
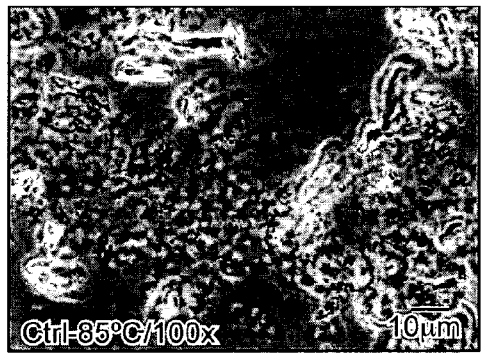
Figure 10B:
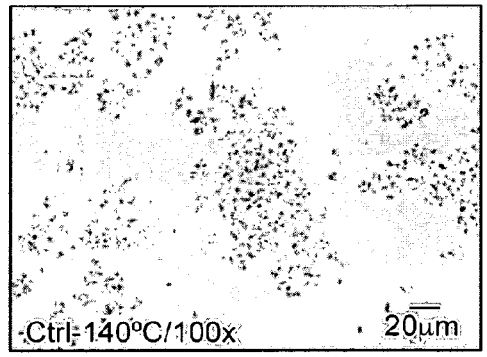
Figure 10C:
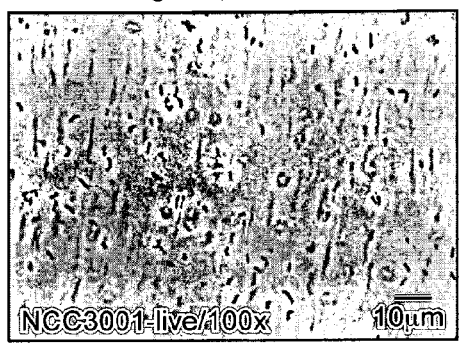
Figure 10C:
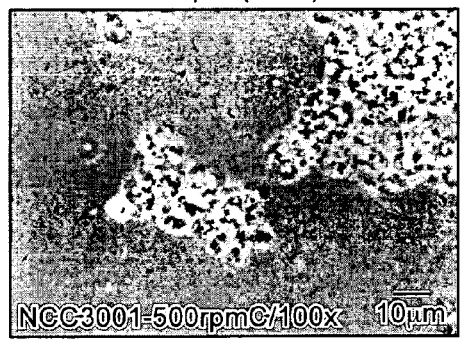
Figure 10C:
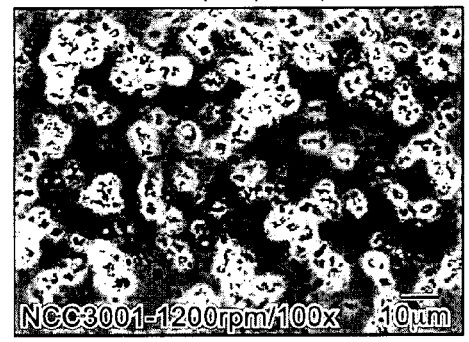
Figure 10C:
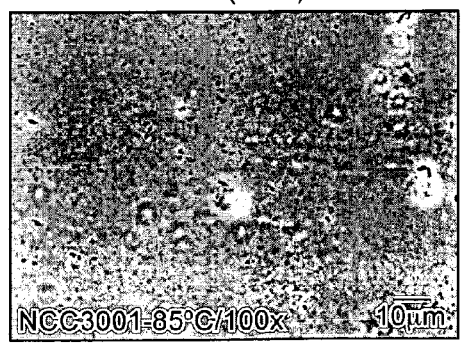
Figure 10C:
Figure 10D:
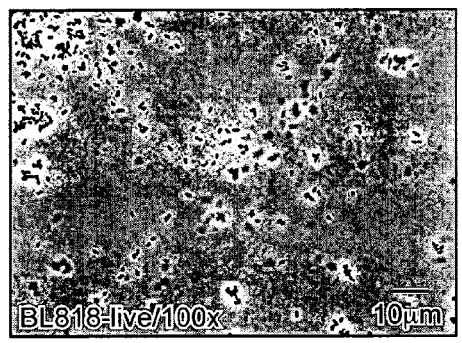
Figure 10D:
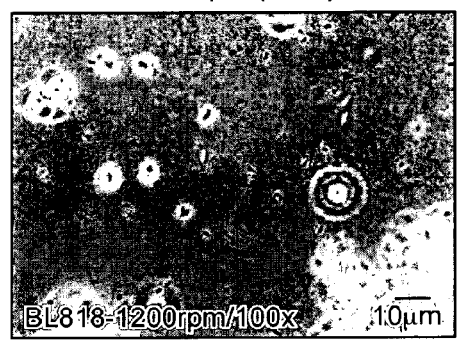
Figure 10D:
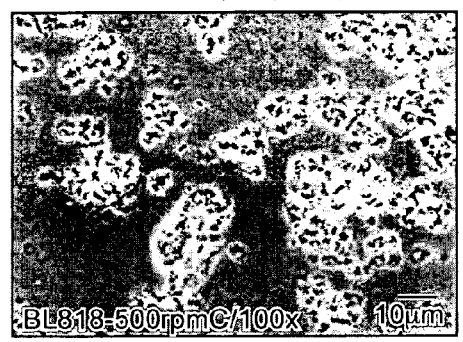
Figure 10D:
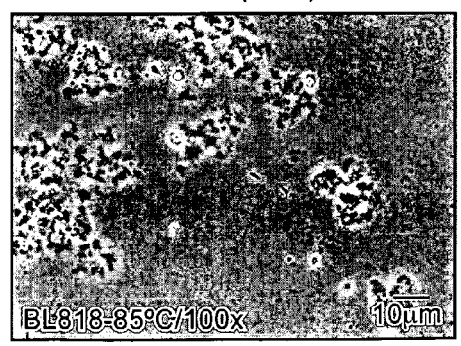
Figure 10D:
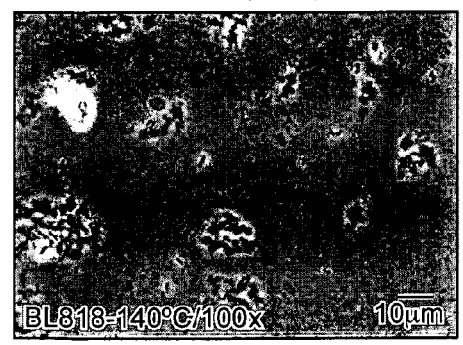
Figure 10E:
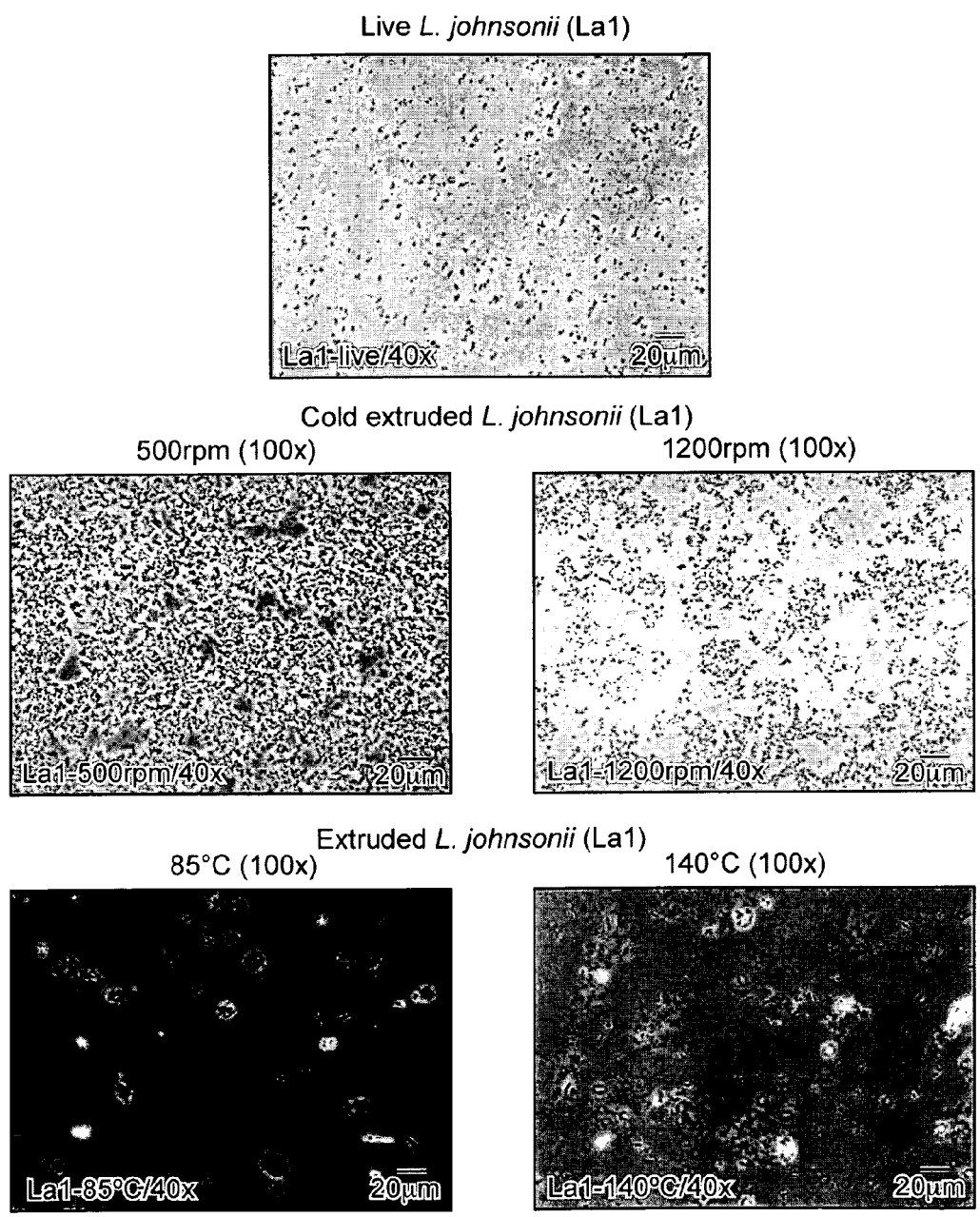
Figure 10F:
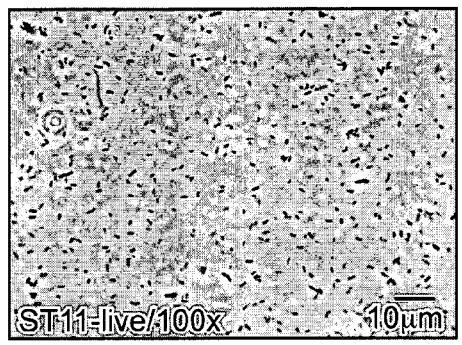
Figure 10F:
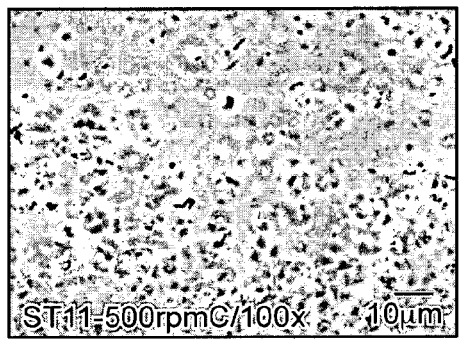
Figure 10F:
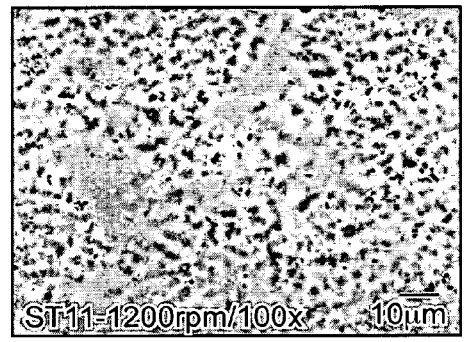
Figure 10F:
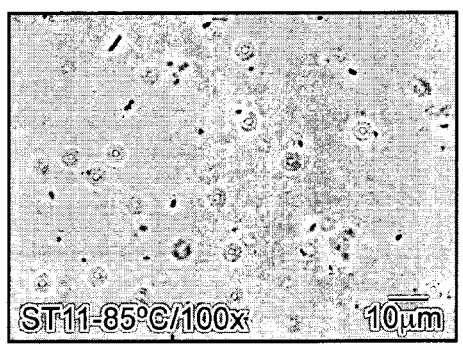
Figure 10F:
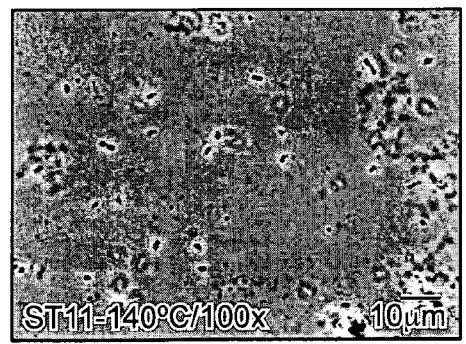
Figure 11A:
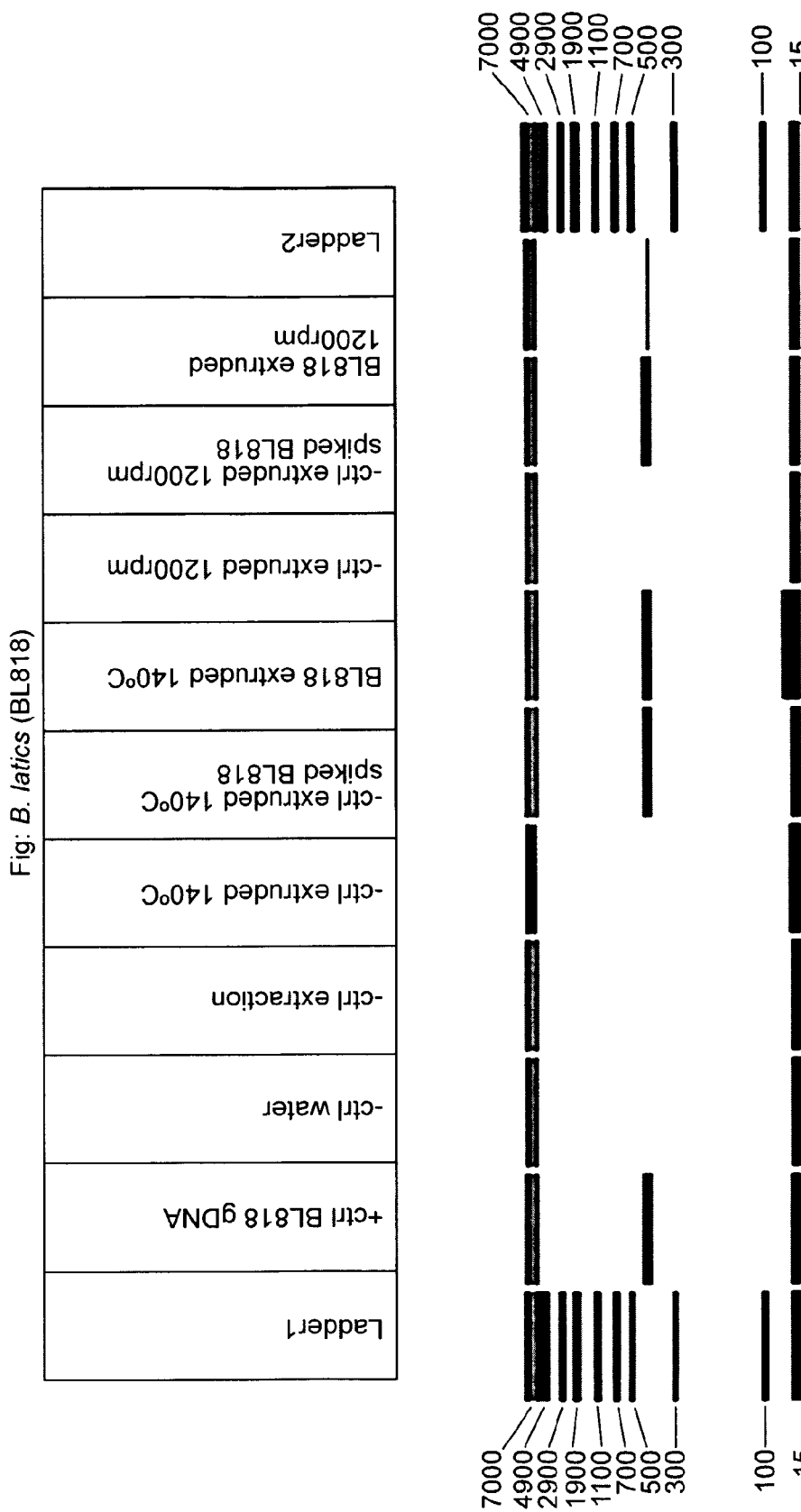
Figure 11A:
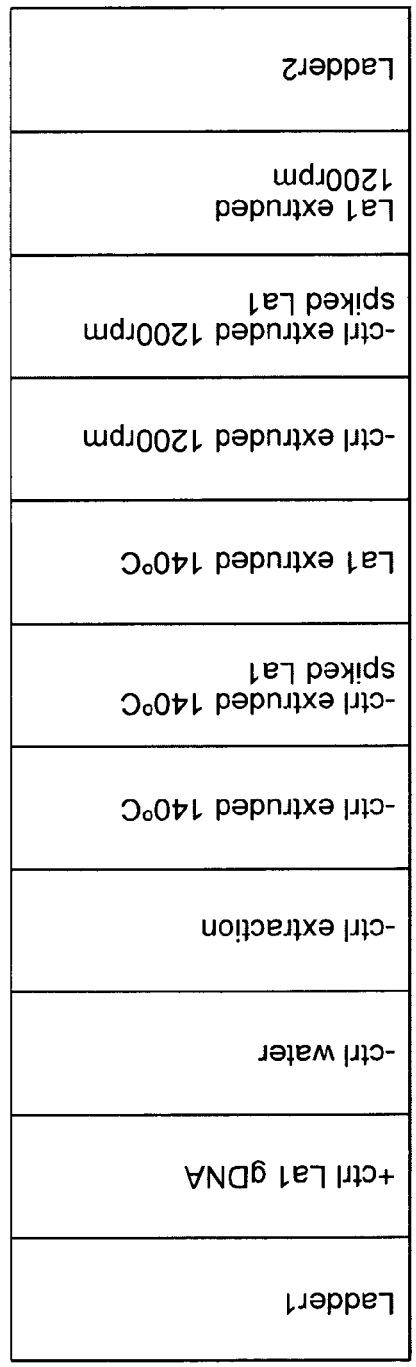
Figure 11A:
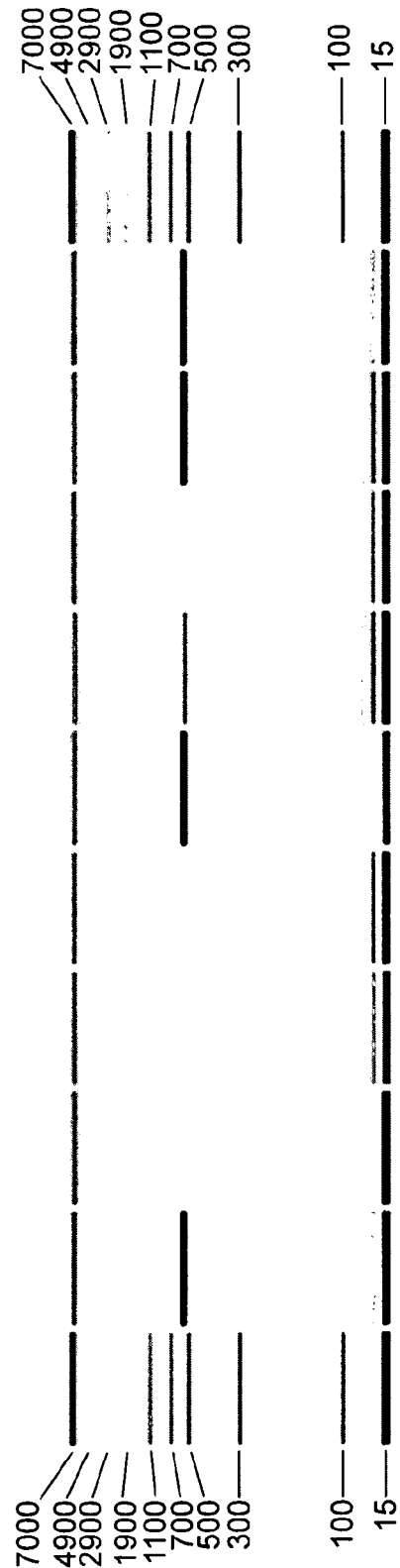
Figure 11B:
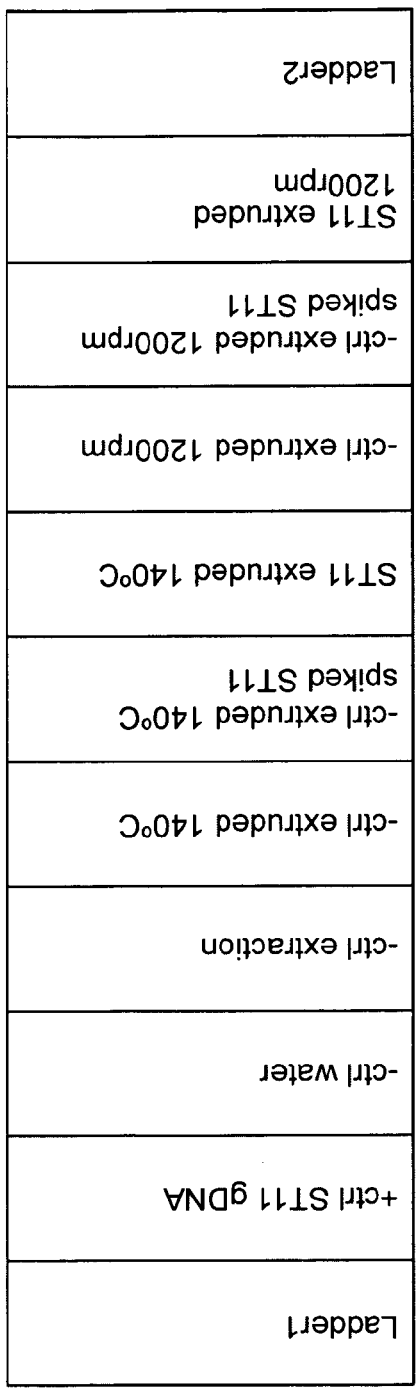
Figure 11B:
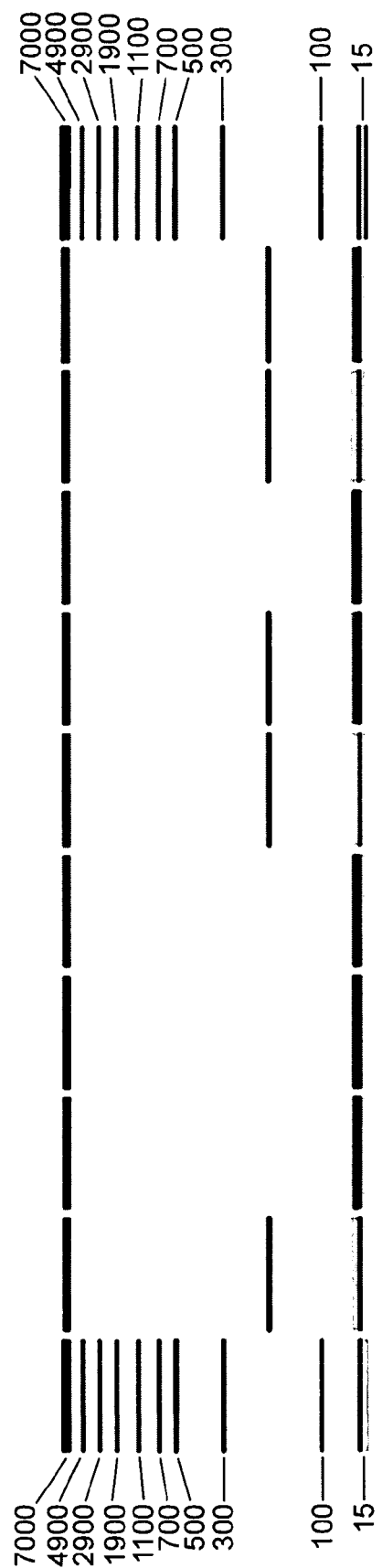
Figure 11C:
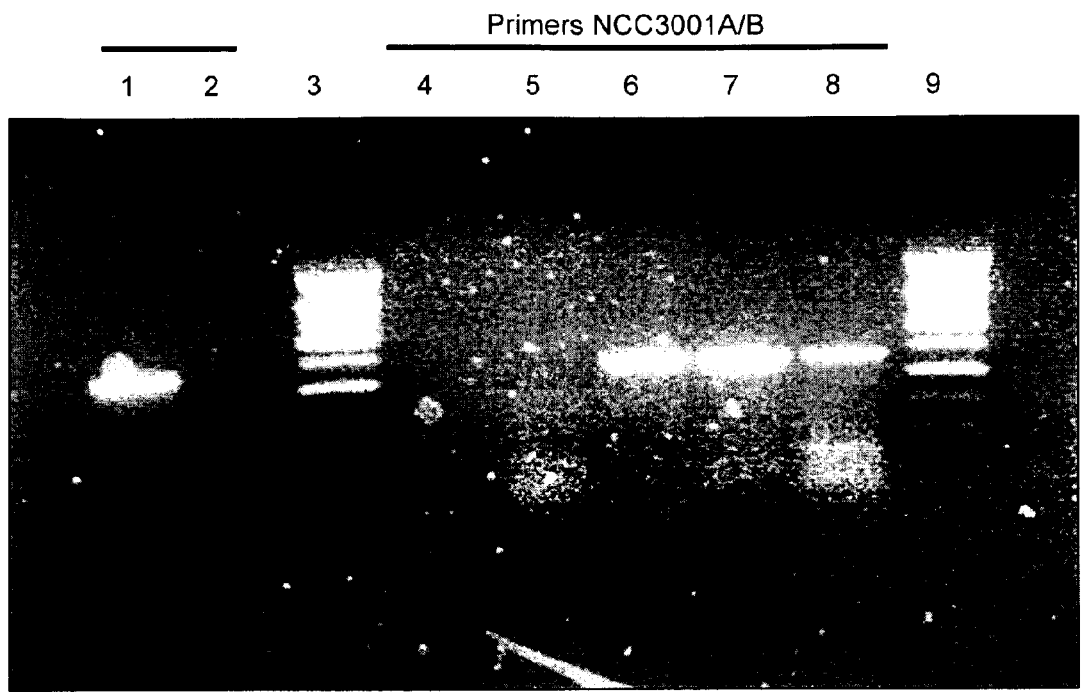

FIG. 9 shows the results of a PCA analysis on cytokine profiles for different extruded preparations of *L. paracasei* ST11.

FIG. 10 shows the detection of bacteria in extruded *B. longum* NCC3001 samples by optical microscopy.

FIG. 11 shows the detection of bacterial DNA in extruded samples by PCR analysis

MATERIALS AND METHODS

Bacterial Preparations:

Powders of *L. rhamnosus* NCC 4007 (CGMCC 1.3724, LPR), *L. paracasei* NCC 2461 (CNCM I-2116, ST11), *B. lactis* NCC 2818 (CNCM I-3446, BL818), *L. johnsonii* NCC 533 (CNCM I-1225, La1) and *B. longum* NCC 3001 (ATCC BA-999, BL999) were re-suspended in phosphate buffer saline (PBS, Sigma) in order to reach a final TS of 35% or a final wet solution containing around $5 \times 10^9$ cfu/ml.

Extrusion Recipes:

Dry mix of rice starch, corn semolina, calcium hydrogen phosphate, calcium carbonate, maltodextrin and milk powder was prepared according to the recipes presented in Tables 1 and 2. All the ingredients were mixed during 30 minutes using a batch mixer [Prodima's mixer, AC-MS (Prodima, St-Sulpice, Switzerland).

TABLE 1

Dry mix recipe used for extrusion (W/W percentage), Example 1

| Ingredients | (Weight in %) |
|---|---|
| Rice starch | 16.0 |
| Corn Semolina | 49.0 |
| Calcium Hydrogen Phosphate | 0.2 |
| Calcium Carbonate | 0.8 |
| Maltodextrin | 17.0 |
| Milk powder | 17.0 |

TABLE 2

Dry mix recipe used for extrusion (W/W percentage), Example 2

| Ingredients | (Weight in %) |
|---|---|
| Rice starch | 8.3 |
| Rice flour | 11.7 |
| Wheat flour | 20.0 |
| Corn Semolina | 58.8 |
| Calcium Hydrogen Phosphate | 1.0 |
| Calcium Carbonate | 0.2 |

Figure 1:
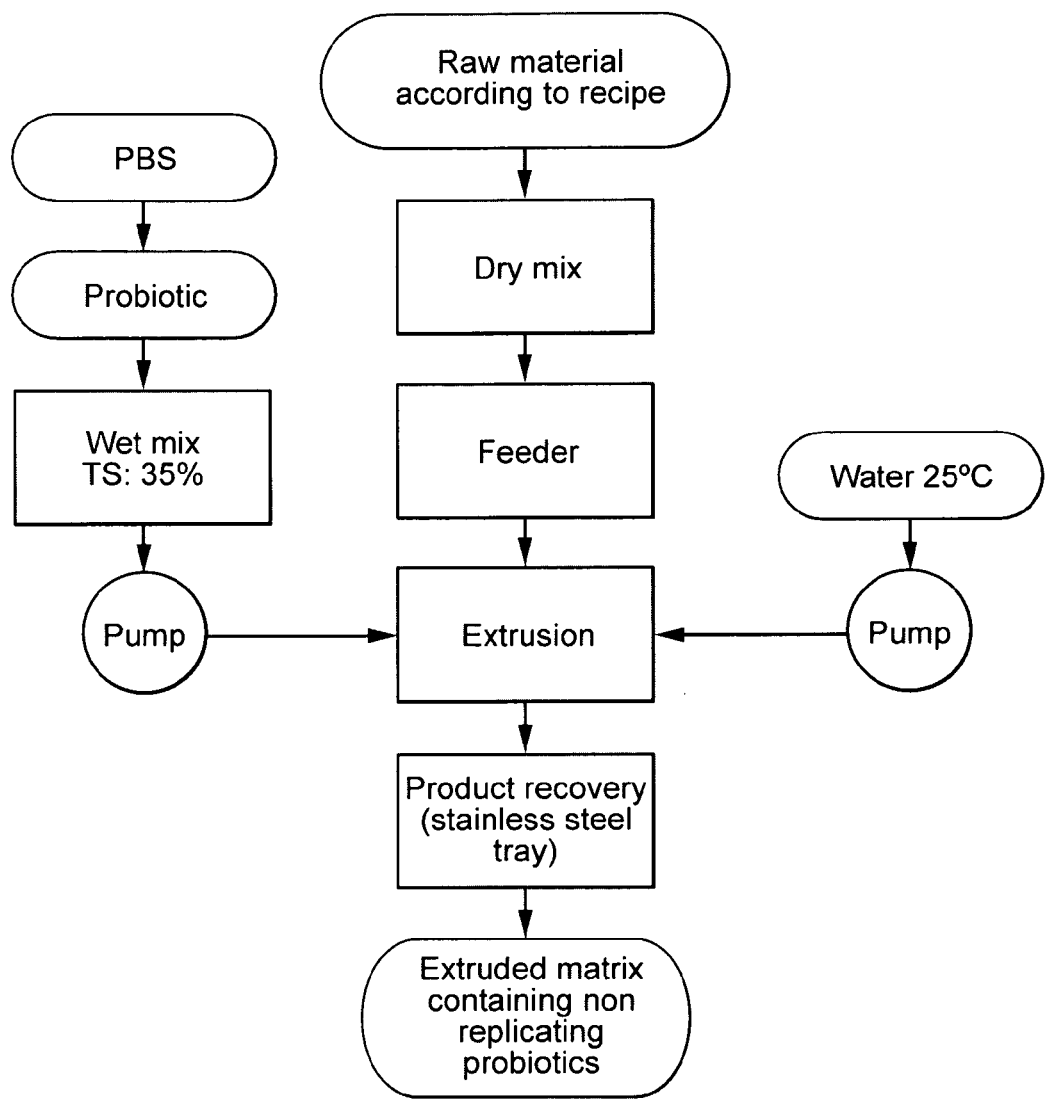
FIG. 1 shows a flowchart of the process used to generate an extruded matrix containing non replicating probiotic micro-organisms (probiotic micro-organisms injected as wet mix into the extruder).

Extrusion:

Experiments were performed using a co-rotating twin-screw extruder (Evolum BC25, Clextral, Firminy, FR) according to the flow chart (FIG. 1). Extrusion temperatures were controlled with six heated sections to reach product temperatures as high as 85, 100, 110, 120, 130, 140 and 160° C. Six barrels were used for the experiments, from n° 1 (feed zone) to n° 6 (before the die channel). Two different kinds of screw elements were used in the axis profile: C2F and C1F. A circular die of 3 mm was used to form extruded tubes. The dry mix was introduced into the extruder feed barrel at a flow rate of 10-12.0 kg/h using a feeder K-Tron (K-Tron, Lenzburg, CH). The bacterial preparation (described above) was injected into the extruder barrel n° 2 using a pump at a flow rate of 0.69-0.87 g/h. Water was injected into the extruder barrel n° 2 at a flow rate of 20-60 mL/min according to the heating temperature. Screw speed was set at 500 rpm. The resulting pressure was between 55 and 125 bars at the die channel. Extruded products containing bacteria were cut by hand and recovered on a stainless steel tray and then conditioned in aluminium bags. Reference control samples were extruded at 85° C., 100° C., 110° C., 120° C., 130° C., 140 or 160° C. in the same conditions without bacteria for analytical needs (hereafter 'extruded control').

Figure 3:
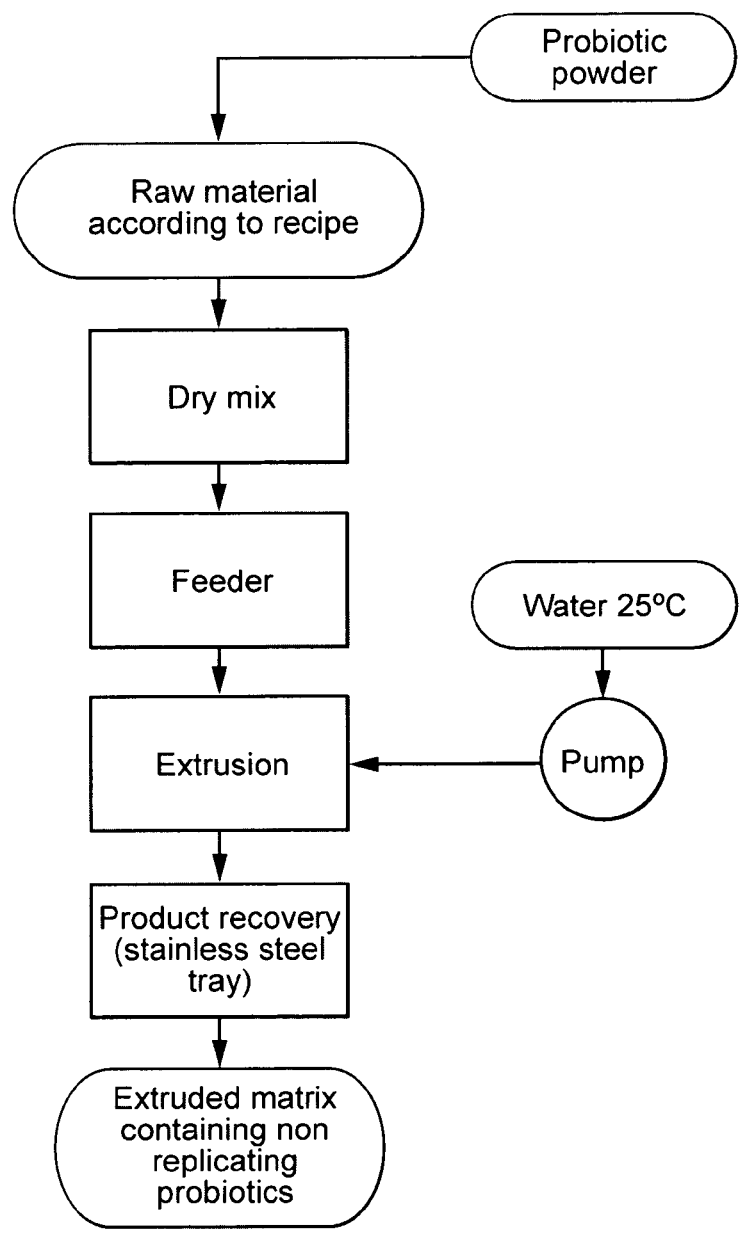
FIG. 3 shows a flowchart of an alternative process that can be used to generate an extruded matrix containing non replicating probiotic micro-organisms (probiotic micro-organisms are part of the dry mix).

An alternative process is shown in FIG. 3 in which probiotics are added into the dry mix recipe (Example 1, Table 1).

Cold Extrusion

Figure 2:
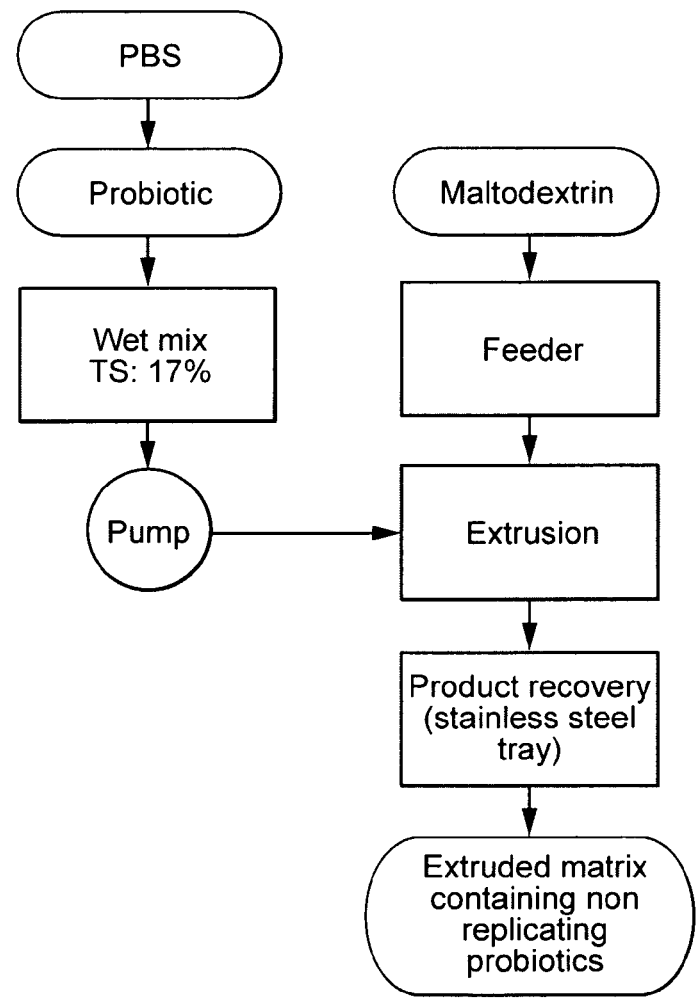
FIG. 2 shows a flowchart of the process used to generate an extruded matrix containing non replicating probiotic micro-organisms (probiotic micro-organisms injected as wet mix into the extruder) using cold extrusion.

Experiments were performed using a co-rotating twin-screw extruder (Evolum BC25, Clextral, Firminy, FR) according the flow chart (FIG. 2). Extrusion temperatures were controlled with six cooled sections to reach product temperatures between 25 and 40° C. Six barrels were used for the experiments, from n° 1 (feed zone) to n° 6 (before the die channel). Two different kinds of screw elements were used in the axis profile: C2F and C1F. A circular die of 3 mm was used to form extruded tubes. The dry mix was introduced into the extruder feed barrel at a flow rate of 8.0 kg/h using a feeder K-Tron (K-Tron, Lenzburg, CH). The bacterial preparation (described above) was injected into the extruder barrel n° 3 using a pump at a flow rate of 2 kg/h. Screw speed was set at 200, 500, 800, 1000 and 1200 rpm.

The resulting pressure was between 1 and 70 bars at the die channel. Extruded products containing bacteria were cut by hand and recovered on a stainless steel tray and then conditioned in aluminium bags. Reference control samples were extruded at 200, 500, 800, 1000 and 1200 rpm in the same conditions without bacteria for analytical needs (hereafter 'extruded control').

Extraction of Bacteria from the Extruded Product:

For Microscopy:

Bacteria were extracted from extruded samples as follows: 25 g of extruded samples were weighed and mixed with 225 ml of trypton salt and antifoam (Sigma). The mix was then mechanically disrupted by stomacher for 90 seconds and incubated at 68° C. for 15 minutes. Two successive filtration steps were then performed through 40 μm and 5 μm filters, respectively. Extruded products not containing probiotics, i.e. "extruded controls" or "controls", were submitted to the same protocol. The filtrated samples, hereafter called "extruded probiotics", were kept at 4° C. until use.

For Human PBMC Cytokine Profiling:

Bacteria were extracted from extruded samples as follows: 10 g of extruded samples were weighed and mixed with 90 ml of PBS (Sigma). The mix was then mechanically disrupted by stomacher for 90 seconds. One filtration step was then performed through a 40 μm filter. Extruded products not containing probiotics, i.e. "extruded controls" or "controls", were submitted to the same protocol and were used as controls in the in vitro assays. The filtrated samples, hereafter called "extruded probiotics", were kept at −20° C. until use.

Bacterial Extraction from Cold Extruded Samples:

Bacteria were extracted from extruded samples as follows: 2 g of extruded samples were weighed and mixed with 18 ml of PBS. The mix was then homogenized for several seconds. Extruded products not containing probiotics, i.e. "extruded controls" or "controls", were submitted to the same protocol and were used as controls in the in vitro assays. The samples, hereafter called "extruded probiotics", were kept at −20° C. until use (human PBMC cytokine immunoprofiling).

Isolation of Human PBMC:

Human peripheral blood mononuclear cells (PBMCs) were isolated from buffycoat from the transfusion center of the CHUV (Lausanne). The cells were diluted 1:2 with Hanks balanced salt solution (HBSS) (Sigma, Lachen, Switzerland). After a Histopaque gradient centrifugation (Sigma), separation by cell density gradient, mononuclear cells were collected at the interface and washed twice with HBSS. Cells were then resuspended in Iscove's Modified Dulbecco's Medium (IMDM, Sigma) supplemented with 10% foetal calf serum (Bioconcept, Paris, France), 1% L-glutamine (Sigma), 1% penicillin/streptomycin (Sigma) and 0.1% gentamycin (Sigma). PBMCs ($7 \times 10^5$ cells/well) were then incubated with different doses of extruded probiotics (doses stated in figures) in 48 well plates for 36 h. The effects of extruded probiotics and extruded controls were assessed on PBMCs from 8 individual donors splitted into two separate experiments. After 36 h incubation, culture plates were frozen and kept at −20° C. until cytokine measurement.

Cytokine Measurements:

Levels of cytokines (IL-12p40, TNF-α and IL-10) in cell culture supernatants after 36 h incubation were determined by electrochemiluminescence based multiplex (MesoScale Discovery, Gaithersburg, Md.) following the manufacturer's instructions. IL-12p40 and TNF-α are pro-inflammatory cytokines, whereas IL-10 is a potent anti-inflammatory and regulatory mediator. Results are expressed as means (pg/ml) +/−SEM of 4 individual donors and are representative of two individual experiments performed with 4 donors each.

PCA Analysis

Numerical cytokine values (pg/ml) determined by multiplex (see above) for each strain were transferred into BioNumerics v5.10 software (Applied Maths, Sint-Martens-Latem, Belgium). A Principal Component Analysis (PCA, dimensioning technique) was performed on this set of data. Substraction of the averages over the characters and division by the variances over the characters were included in this analysis. Strains inducing high levels of pro-inflammatory cytokines cluster in the right side of the graph, as opposed to strains inducing high amounts of anti-inflammatory cytokines that cluster in the left side panel.

Optical Microscopy

Bacteria were extracted from extruded samples as previously described in the section "Extraction of bacteria from the extruded product" with some changes. Samples were submitted to enzymatic digestion by alpha-amylase for 1 hour at 68° C. prior to filtration step followed by optical microscopic observations (magnification 40× and 100×).

For PCR Analyses:

DNA Extraction of Extruded Bacteria for PCR:

DNA was extracted from extruded samples using the QIAquick and QIAamp (Qiagen) kit following the supplier instruction with the following modification. 2 g of extruded samples were weighed and mixed with 10 ml of CTAB (Hexadecyltrimethyl-ammonium bromide) (AppliChem) and 225 ul of protease (Qiagen) to obtain a final concentration of 450 μg/ml. Then the mix was incubated in a water bath for 1 hour at 65° C. The preparation was centrifuged and the aqueous phase was collected and mixed with an equal volume of chloroform (Merck). After centrifugation, the supernatant was transferred with 5 volumes of PB Buffer (Qiagen) on a QIAamp Maxi column, attached to a vacuum pump at a maximum of −600 mbar. The column was washed twice with PE buffer (Qiagen) and dried by centrifugation. The purified DNA was eluted with 1 ml of EB buffer (Qiagen) for 5 minutes and recovered after centrifugation. A second purification was done as previously using the eluted DNA with a QIAquick column (Qiagen).

Polymerase Chain Reaction (PCR)

PCR were carried out in a Thermocycler (GeneAmp PCR System 9700, Applied Biosystem). 1 μl of DNA purified were added in 24 μl of amplification mixture. Amplification were carried out in 0.2 ml Thermo-Strip tubes containing the reaction buffer: each dATP, dCTP, dGTP, dTTP nucleotide (Roche Applied Science) at 2.5 mM, 10 pmol/μl of each specific primer, 2.5 μl of 10× PCR buffer containing 15 mM MgCl2 (Applied Biosystem), 1.25 units of AmpliTaq Gold (Applied Biosystem), and Nuclease free water. 30 cycles of amplification were performed, each cycle consisting of denaturation step (30 sec at 94° C.) followed by an annealing step of 30 seconds at (60° C.) and an elongation step (30 sec at 72° C.). The elongation step was extended to 7 minutes at 72° C. during the last cycle. The PCR products were then analysed by agarose gel electrophoresis or by Automated Electrophorectic Separations (LabChip GXII, Caliper)

Electrophoresis:

PCR products were visualized on agarose gel.

10 μl of the PCR product were mixed with 2 μl of blue loading buffer and loaded on a 1.2% agarose gel containing 1×SYBR Safe. Samples and a molecular weight ladder were run for 1 hour at 80V. Pictures of the gel were taken with UV illumination.

Automated Electrophoretic Separation of DNA:

DNA chip was prepared by adding Gel-Dye and DNA marker (Caliper). PCR products were transferred into a 96 well plate and loaded in the LabChip GXII. Samples were detected by laser-induced fluorescence and data were automatically analyzed with System software providing the size (pb) and the quantity (ng/μl) of the product. Results were reported as virtual gel.

Results

The immune profiles of extruded samples of *B. longum* NCC3001 were assessed in vitro using the PBMC assay. Pro-inflammatory (TNF-α and IL-12p40) and anti-inflammatory (IL-10) cytokines were measured in cell culture supernatants after 36 h incubation. Control extruded products without bacterial supplementation induced low levels of pro- and anti-inflammatory cytokines (FIG. 4). Inclusion of live *B. longum* NCC3001 in the extrusion process (temperature of 130° C.) dramatically stimulated the production of cytokines in a dose dependent manner. The best cytokine induction was found at a dose of about $10^8$ equivalent cfu/ml (FIG. 4).

We then addressed the question whether extrusion at different temperatures (110° C. and 120° C.) would lead to similar in vitro immune activation. We therefore compared the samples resulting from extrusion at three different temperatures at the dose of $10^9$ equivalent cfu/g. As shown in FIG. 5, all extruded samples containing B. longum NCC3001 efficiently activated immune blood cells, as compared to the control. Temperatures applied during the extrusion did not seem to impact on the immune profiles of extruded B. longum samples since relatively high levels of cytokines were induced at each temperature tested (FIG. 5). B. longum NCC3001 was added as live bacteria ($10^{10}$ cfu/mL) into the extruder as shown in FIG. 1. We checked the residual viable counts at the end of the process by plating samples on MRS+ Cysteine agar. All the added bacteria were rendered non replicating by the process since no colonies were observed in any samples extruded at 110° C., 120° C. and 130° C. (data not shown). The presence of rod shaped bacteria in extruded B. longum NCC3001 containing products (magnitude 100×) as opposed to the control sample (FIG. 10), allowed us to conclude that the in vitro immune activation previously described with extruded B. longum NCC3001 samples is therefore due to the presence of non viable bacteria in the final products.

We then addressed the question whether extrusion of different strains, at different temperatures (from 85° C. to 140° C.) and at different screw speeds (from 200 rpm to 1200 rpm) would lead to similar in vitro immune activation. We therefore compared the samples resulting from extrusion of 4 additional strains at five different temperatures and five different screw speeds at the dose of $10^9$ equivalent cfu/g. As illustrated in FIG. 6 extruded samples containing non replicating L. paracasei NCC2461 (ST11), and B. lactis NCC2818 (BL818) and L. johnsonii NCC533 efficiently activated immune blood cells, as compared to the controls. These data are in agreement with the data previously found for B. longum NCC3001 (FIG. 4). Temperatures applied during the extrusion—i.e hot or cold extrusion—did not seem to impact on the immune profiles of extruded B. longum samples since relatively high levels of cytokines were induced at each temperature tested (FIG. 5). Likewise, screw speeds above 600 rpm allowed generating non replicating strains (no cfu detectable by plating) that were still triggering the immune cells (FIGS. 7 and 9). So mechanical shearing, independently of temperature, can be used to render probiotics non replicating while maintaining their capacity to stimulate immune cells.

PCA analyses revealed that extruded bacteria triggered immune cell activation in vitro (FIGS. 7, 8 and 9). However, extruded and live bacteria were found in separate clusters, indicating that the extruded bacteria are able to exhibit improved or newly acquired immune properties, as compared to live controls.

Rod shapes were detected by microscopy in all samples extruded with the different probiotic strains, but not in their respective controls (for examples see FIG. 10). The presence of the probiotic strains in extruded samples was validated by PCR analysis using strain specific probes (FIG. 11). For example, chromosomal DNA of L. paracasei NCC2461, B. longum NCC3001, B. lactis NCC2818 and L. johnsonii NCC533 was detected, as shown by specific bands on virtual gel or on agarose gel.

Probiotic bacteria were added as live bacteria ($10^{10}$ cfu/mL) into the extruder in FIGS. 1 and 3. We checked the residual viable counts at the end of the process by plating samples on MRS+/− Cysteine agar. All the added bacteria were rendered non replicating by the process since no colonies were observed in any samples extruded at temperatures from 85° C. to 160° C. and 140° C. and cold extruded at a screw speed from 800 rpm to 1200 rpm (data not shown). The presence of rod shaped bacteria in extruded products (magnitude 100×) as opposed to the control samples (FIG. 10), allowed us to conclude that the in vitro immune activation observed in response to extruded products is therefore due to the presence of non viable bacteria in the final products.

As a result, we showed that extrusion of raw materials with live probiotic bacteria at different temperatures and shearing conditions led to extruded products containing non replicating probiotic microorganisms with immune stimulating activities. To our best knowledge, the process of extrusion has never been reported for generation of non viable non-replicating probiotics that are still able to activate the immune system. The concept can be generalized to any probiotic bacterium or dairy starters and any extrusion temperatures or conditions. This invention thus describes a novel way of generating non replicating probiotics that deliver health beneficial properties and leads to new concepts of extruded products. In particular, the present invention also describes a novel way of generating non replicating probiotics that exhibit improved or newly acquired immune stimulating activities.

The invention claimed is:

1. A method for making a composition comprising probiotic micro-organisms rendered non-replicating, the method comprising extruding the probiotic micro-organisms by direct expansion extrusion cooking at a temperature between 110 and 180° C. and at a moisture content below 20 wt %, wherein the probiotic micro-organisms are selected from the group consisting of Bifidobacterium longum NCC 3001, Bifidobacterium longum NCC 2705, Bifidobacterium breve NCC 2950, Bifidobacterium lactis NCC 2818, Lactobacillus johnsonii NCC533, Lactobacillus paracasei NCC 2461, Lactobacillus rhamnosus NCC 4007, Lactobacillus reuteri DSM17938, Lactobacillus reuteri ATCC55730, Streptococcus thermophilus NCC 2019, Streptococcus thermophilus NCC 2059, Lactobacillus casei NCC 4006, Lactobacillus acidophilus NCC 3009, Lactobacillus casei ACA-DC 6002 (NCC 1825), Escherichia coli Nissle, Lactobacillus bulgaricus NCC 15, Lactococcus lactis NCC 2287, and combinations thereof.

2. The method of claim 1, wherein the probiotic micro-organisms are co-extruded with other parts of the composition.

3. The method of claim 1 comprising adding probiotic micro-organisms to a raw material by dry mixing, extruding the dry mix under water addition, and recovering the extruded material comprising the non replicating probiotic micro-organisms.

4. The method of claim 1 comprising adding a wet mix comprising water and probiotic micro-organisms during an extrusion step to a raw material in powder format, and recovering the extruded material comprising the non replicating probiotic micro-organisms.

5. The method of claim 1, wherein the direct expansion extrusion cooking occurs at a pressure from 100 to 150 bars.

* * * * *